(12) United States Patent  
Amery et al.

(10) Patent No.: US 6,613,325 B1
(45) Date of Patent: Sep. 2, 2003

(54) PREVENTION OF POST SURGICAL ADHESIONS USING A FIBRIN MONOMER SEALANT

(75) Inventors: Michael J. Amery, Washington Crossing, PA (US); Paul Sibbons, Harrow (GB); Stuart Burnett, Liverpool (GB); Sally-Anne Rickets, Amersham (GB); Peter A. D. Edwardson, Leeds (GB); Jonathan Hughes, Buckinghamshire (GB); Derek A. Hollingsbee, Neston (GB); Stewart A. Cederholm-Williams, Oxford (GB); Horace R. Trumbull, Skillman, NJ (US); Herman Eugene Griffin, Wakefield, RI (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/585,030

(22) Filed: Jun. 1, 2000

Related U.S. Application Data

(60) Provisional application No. 60/136,901, filed on Jun. 1, 1999.

(51) Int. Cl.[7] .................. A61K 38/48; A61K 31/74; A61F 13/00
(52) U.S. Cl. .................. 424/94.64; 424/78.06; 424/77; 424/423; 424/422
(58) Field of Search .................. 424/94.64, 529, 424/530, 78.06, 682, 422, 423, 77; 514/21, 12

(56) References Cited

U.S. PATENT DOCUMENTS

| | | | | |
|---|---|---|---|---|
| 5,702,715 A | | 12/1997 | Nikolaychik et al. | 424/402 |
| 5,763,410 A | * | 6/1998 | Edwardson et al. | 514/21 |
| 5,795,584 A | | 8/1998 | Totakura et al. | 424/426 |
| 6,054,122 A | | 4/2000 | MacPhee et al. | 424/94.4 |
| 6,056,970 A | * | 5/2000 | Greenawalt et al. | 424/426 |

* cited by examiner

Primary Examiner—Thurman K. Page
Assistant Examiner—Blessing Fubara
(74) Attorney, Agent, or Firm—John M. Kilcoyne

(57) ABSTRACT

In accordance with the present invention it has been found that a fibrin polymer film formed by applying materials most closely resembling the natural clotting materials to a surgical adhesion formation. Preferred embodiments involve application of a fibrin monomer under polymerizing conditions to the surgical wound site. Unexpectedly, in addition to this improved prevention of adhesions, the more chemically-natural clots, especially the fibrin-monomer based fibrin polymer, also functions as a fibrin sealant, i.e., has adherence, provides hemostasis and promotes wound healing while also functioning as a barrier. In preferred embodiments the novel methods of this invention conveniently use one or more plasma proteins derived from the patient's own blood as to be autologous. Further, the sealant material is preferably substantially free of any added or exogenous enzymes, e.g., thrombin, etc., which catalyze the cleavage of fibrinopeptides A and/or B from fibrinogen. Preferably a fibrin monomer solution is sprayed over the wounded surgical site.

8 Claims, 12 Drawing Sheets

BOX AND WHISKER PLOT OF RAW DATA. THE BOXES CORRESPOND TO THE INTERQUARTILE RANGE (THE CENTRAL 50% OF THE DATA). THE SOLID INTERNAL LINE REPRESENTS THE MEDIUM VALUE. THE DOTTED HORIZONTAL LINE IS THE MEAN VALUE. THE LENGTH OF THE WHISKERS ARE PLOTTED INDIVIDUALLY. POINTS OUTSIDE THESE ARE INDIVIDUALLY GRAPHED.

PREVENTION OF POST SURGICAL ADHESIONS USING A FIBRIN MONOMER SEALANT

This application claims the benefit the of Provisional Application No. 60/36,901, filed Jun. 1, 1999.

FIELD OF THE INVENTION

This invention relates to the prevention of post surgical adhesions and, more particularly, concerns enhanced methods and compositions using a fibrin sealant to prevent such adhesions.

BACKGROUND OF THE INVENTION

Formation of tissue adhesions between adjacent tissues is an adverse side effect of many surgical procedures. It is believed that following abdominal surgery the incidence of peritoneal adhesion formation may be as high as 90%. These post surgical adhesions often lead to pain, discomfort, immobility and, in the case of gynecological surgery, female infertility. Also, post surgical adhesions may even result in life-threatening bowel strangulation is some instances. Thus, there exists a large unmet need for a way to prevent post surgical adhesions, given the potential discomfort and medical risks they pose following routine surgery and the accompanying financial burden of remedying this adverse effect.

A number of pathways have been investigated to reduce or prevent post surgical adhesions. One proposed mechanism involves the reduction of the inflammatory reaction at the wounded site following surgery. In this regard, the use of corticosteroids, NSAIDS, histamine antagonists and calcium channel blockers has been suggested. Another prevention method recommends the inhibition of coagulation at the wounded site using, e.g., heparin or oral anticoagulants. Still further methods entail the promotion of fibrinolysis through appropriate administration of, for example, fibrinolysin, Streptokinase, Urokinase and t-PA. More recently, barrier materials have been suggested for the prevention of post surgical adhesions. The include, but are not limited to, amniotic membrane, rubber, silver foil, Teflon, dextran, hyaluronic acid, Surgigel® (regenerated cellulose), Interceed® (TC7 oxidized, regenerated cellulose), Polaxamer 407 (temperature dependent polymer), Gore-Tex® (expanded polytetrafluorethylene) and SepraFilm® (hyaluronic acid derivative film).

The above materials and methods fall into two basic categories; those which do not work effectively, and those which may provide some efficacy but are limited in either their use or applicability. Accordingly, new efforts have continued in this area.

The role of fibrin sealants in surgical procedures generally has been reviewed for many years. The role of fibrin sealants preventing or reducing of post surgical adhesions has been investigated over the past few years and is not totally understood at this time. Indeed, the literature in this area seems somewhat divided. Several researchers have reported an improvement in post surgical adhesion prevention using fibrin sealants. For example, the incidence of parovarian adhesions was significantly reduced in women subjected to laser vaporization of endometriomas and fibrin sealant (Donner, J. et al.; *J Gynecol Surg* 7:163, 1991), incisioned and colonic adhesions formation was reduced in abraded rabbit uterine horns (Chmielewski, G. et al.; *The American Surgeon* Vol 58 No. 9; 590, 1992), intrabdominal adhesion formation was reduced in rats (deVirgilio, et al.; *Aarch Surg* Vol 125; 1378, 1990), epidural scar formation in rats was reduced after laminectomy (Vaquero, J. et al.; *Acta Neurochir* (Wien) 120; 159–163, 1993) and flexor tendon adhesion formation in rabbits was reduced following a partial laceration of the flexor tendon (Fryknra, E. et al.; *Journal of Hand Surgery* Vol. 18A, No. 1; 68, 1993).

Others reporting on the use of fibrin sealants to prevent post surgical adhesions have not been so positive. For example, fibrin sealant was found to have no statistically significant effect in preventing perivascular adhesions following arteriotemics of the femoral and carotid arteries of dogs (Dickinson, C. et al., *Vascular Surgery*; 15, 1993); fibrin sealant did not prevent adhesion formation in colonic anastomoses in the rat (van der Ham, A., et al.; *J Surgical Research*, 55; 256–260, 1993) and fibrin sealant did not reduce post surgical adhesions following ovarian reconstruction in the rabbit (Bilgin, T., et al.; *Gynecol Obstet Invest* 39; 186–187, 1995).

WO 92/22312 to Wadstrom discloses combinations of fibrin sealants and biocompatible polymers reportedly useful for the prevention of post surgical adhesions. WO 92/22312 reports that fibrin sealants alone provide a wound healing effect which results in strong scar formation and does not prevent adhesions. The viscosity enhancing polymers are useful to allow application of the otherwise watery sealant components to vertical surfaces and also prevents adhesions. These polymers are high molecular polyglycans or polysaccharides.

WO 96/22115 discloses a self supporting sheet material of cross-linked fibrin having a particular range of pore sizes to prevent or reduce post surgical adhesions. The use of spray application to prepare these and similar sheets is reported in WO 98/02098. These sheets are described as generally non-adherent and non-hemostatic and are preferably used in conjunction with a known fibrin sealant which does possess adherence and hemostatic capabilities. These sheets are prepared using high concentrations of fibrinogen and high dose thrombin to obtain the desired structure regarding pore size and distribution (preferably <20 $\mu$m, more preferably <5 $\mu$m, most preferably <1 $\mu$m). Also, the sheet is pre-formed outside of the body and needs to be applied as a solid material, i.e., not applied as a spray or liquid.

Since fibrin sealants are used increasingly for hemostasis and fluid and air leakage in surgical procedures, it is important that a sealant is used which does not promote adhesion formation. Also, since fibrin is a part of the natural healing process it seems desirable to attempt to use fibrin in resolving the post surgical adhesions problem, as well. It would be preferable to be able to accomplish this without polymer additives, without high concentrations of fibrinogen, without subjecting the patient to high dose thrombin and, preferably, without the need for preformed sheets which must, in turn, be used with standard sealants. A more natural, single-step sealant/hemostat/adherent/adhesion barrier, preferably applicable by spraying and preferably free of added thrombin would be a significant advance in the art.

SUMMARY OF THE INVENTION

Figure 1:
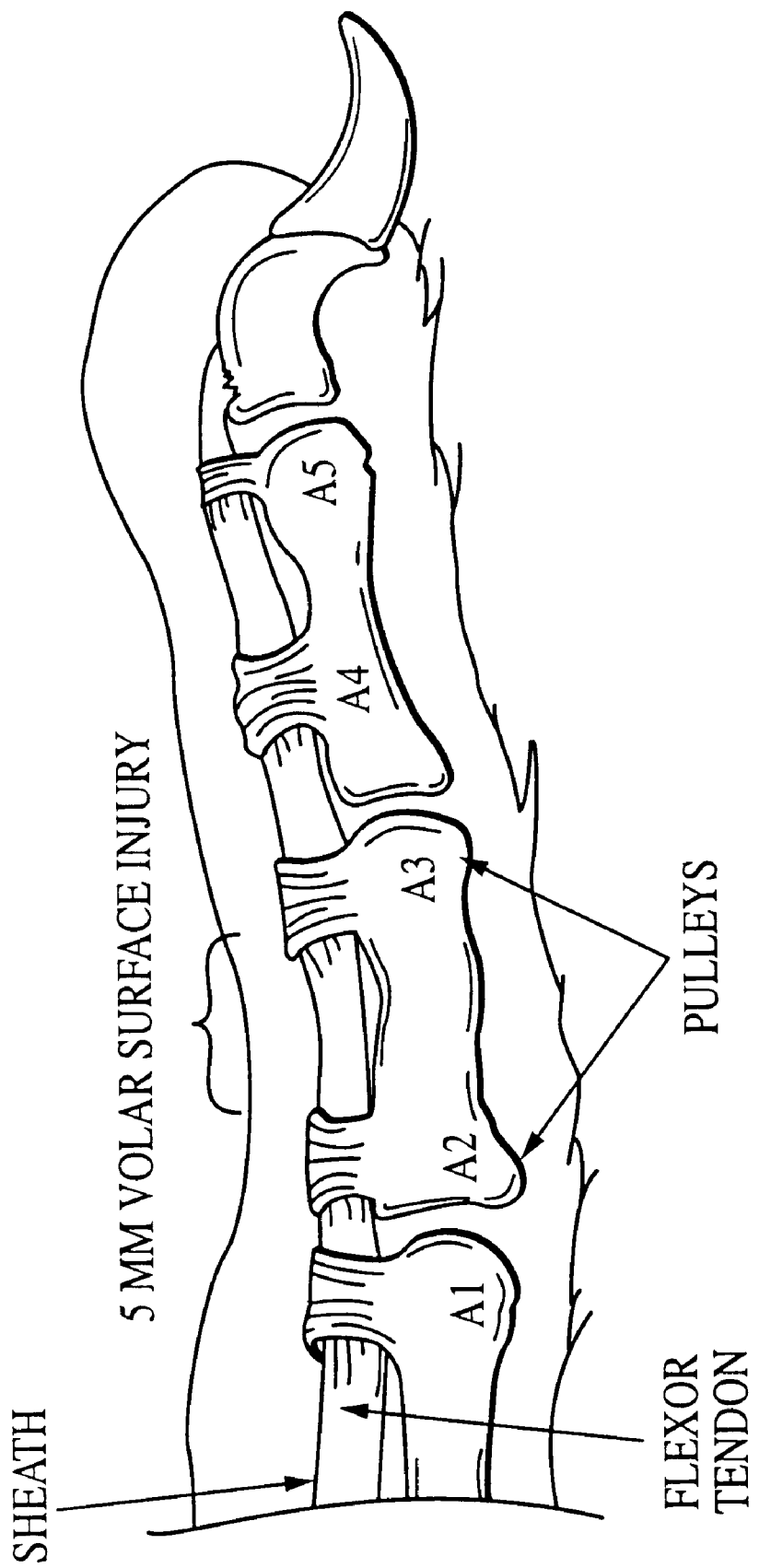
FIG. 1 Illustrates a rabbit paw flexor tendon per the experiments of Example 2.
Figure 2:
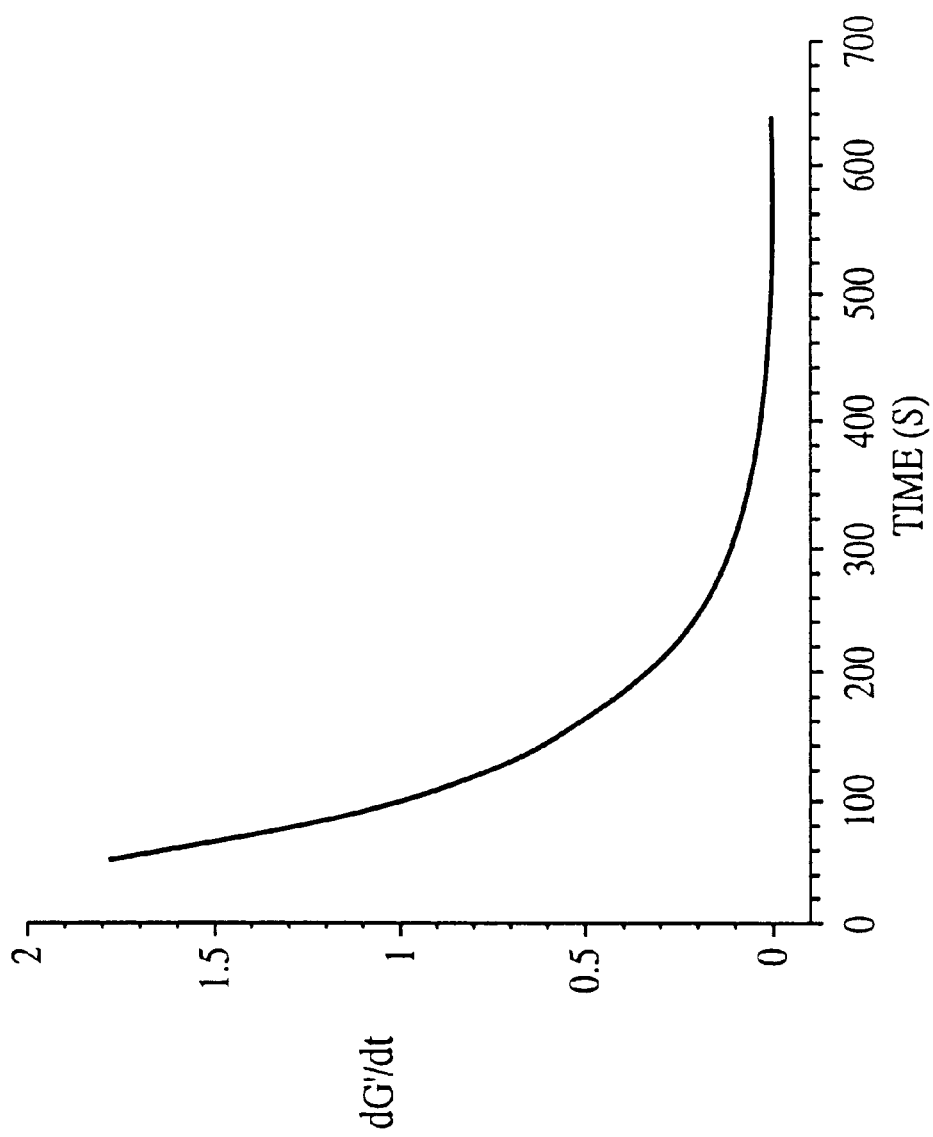
FIG. 2 Is a graph showing variation of dG'/dt with time per Example 2.

In accordance with the present invention it has been found that a fibrin polymer film formed by applying materials most closely resembling the natural clotting materials are useful in a method to prevent or reduce the incidence of surgical adhesion formation. Preferred embodiments involve application of a fibrin monomer under polymerizing conditions to the surgical wound site which fibrin is preferably patient-derived, i.e., a sealant wherein the blood/clotting components are autologous to the patient. Unexpectedly, in addition to this improved prevention of adhesions, the more chemically-natural clots, especially the fibrin-monomer based fibrin polymer, also functions as a fibrin sealant, i.e., has adherence, provides hemostasis and promotes wound healing while also functioning as a barrier. In preferred embodiments the novel methods of this invention conveniently use one or more plasma proteins in addition to fibrinogen/fibrin derived from the patient's own blood so as to be autologous. Further, the sealant material is preferably substantially free of any added or exogenous enzymes, e.g., thrombin, etc., which catalyze the cleavage of fibrinopeptides A and/or B from fibrinogen. Preferably a fibrin monomer solution is sprayed over the wounded surgical site.

DETAILED DESCRIPTION OF THE INVENTION

The present invention is founded upon the idea that providing a fibrin polymer which can act as a barrier, while most closely resembling the natural clotting materials, provide enhanced reduction in the incidence of post surgical adhesion formation. The enhancement can be realized as increased convenience and/or diminished immunogenic or inflammatory response and/or superior post surgical adhesion prevention. The methods of the present invention rely, therefore, on several factors which individually provide improvements over the prior art and which cumulatively provide an optimum result. The factors, in no particular order, include applying fibrin monomer instead of fibrinogen, using fibrin substantially free of thrombin or other fibrinopeptide-cleaving enzyme, using autologous fibrin, using freshly prepared fibrin which has not been denatured in processing, using fibrin with co-harvested plasma proteins, using fibrin with lower concentrations and eliminating the need for polymer additives.

Accordingly, methods employing one, some or all of these aspects are considered to be a part of the present invention.

As mentioned above, it has been found that the fibrin polymer resulting from the present methods is able to reduce or prevent post surgical adhesions over a variety of fibrin concentrations and need not be a high concentration material when compared to the prior art. Further, there is no need to pre-form sheet-like materials ex vivo for application to a surgical wound site and no need for additional sealant layers to be used. The present fibrin sealants, when applied using the methods described herein, possess not only good barrier qualities to resist post surgical adhesion formation but also provide hemostasis, fluid sealing, adherence to the tissue and enhanced cell migration at the wound site. This enhanced cell migration is believed to provide improved angiogenesis and tissue repair.

In one embodiment of the present invention an improved method of preventing or reducing the incidence of post surgical adhesions involves using a fibrin polymer formed from a fibrin monomer composition. This, in turn, can be conveniently accomplished by applying, e.g., spraying, a fibrin monomer composition onto the surgical wound site under polymerizing conditions to form the fibrin polymer. The fibrin monomer composition has the advantage that it can polymerize much more rapidly than prior art fibrinogen/thrombin systems and does not therefore require added polymer, as in WO 92/22312 to Wadstrom, or "pre-form" time as in WO 98/02098 in order to set up and stay in place even on vertical surfaces. This more rapid polymerization is because the fibrin monomer has had at least one of the fibrinopeptides of fibrinogen already cleaved and polymerization can begin virtually immediately. U.S. Pat. No. 5,750,657 to Edwardson et al. Describes a preferred fibrin monomer composition which is "nondynamic", i.e., prepared such that it is inhibited from polymerizing until the nondynamic conditions are reversed. A preferred way to render fibrin monomer nondynamic is to prepare it as a low pH composition. For example, aqueous fibrin monomer solutions having pH 2–5 are suitable. These can be co-applied with sufficient higher pH buffer, e.g., a pH 10 buffer, to raise the pH and trigger the fibrin monomer polymerization. The advantages of the fibrin monomer method include the multifunctional aspects of the resulting single polymer, i.e., hemostat/fluid seal/adhesive/barrier, and the advantage that no added or exogenous thrombin is required. Also, lower fibrin concentrations, on the order of 10–30 mg/ml and preferably 15–25 mg/ml, are not only adequate, but preferred. Although any fibrin monomer concentration greater than 10 mg/ml, e.g., 10–200 mg/ml, could be used. If it is desired to make an ex vivo preformed sheet, the fibrin monomer method is still advantageous for the reasons mentioned above. In either case, the fibrin monomer can be, fibrin I, fibrin II, des ββ fibrin or mixtures of any of these depending upon the enzyme used (thrombin or other enzyme which catalyzes the cleavage of fibrinopeptide A and/or B from fibrinogen). Preferably, especially in the case of thrombin, the enzyme is removed from the fibrin monomer composition. Additional parameters for preparing and applying fibrin monomer solutions are known from U.S. Pat. No. 5,750,657 to Edwardson et al., an exemplary combination being the co-application of a pH 4 aqueous solution of 15–25 mg/ml of fibrin I monomer with pH 10 acetate buffer in a ratio of 7:1 fibrin to buffer.

As discussed above, the fibrin monomer method provides the option that a fibrin polymer can be applied and used in the present methods while avoiding application of thrombin or thrombin-like enzyme to the patient. This turns out to be an enhanced method in and of itself. That is, prevention or reduction of the incidence of post surgical adhesions using fibrin polymer/fibrin sealant materials is enhanced where no added or exogenous thrombin or thrombin-like enzyme are used. It has been found that high dose thrombin as is used in prior art sealant methods and the prior art post surgical adhesion reduction methods as described in WO 96/22115 and WO 98/02098 may cause an inflammatory response in tissues, organs and, particularly, wound sites. In a surgical wound site it is believed that added thrombin can cause an inflammatory response which may itself be negative and which may indirectly "kick-start" the wound healing process before the prior art sealant has polymerized sufficiently to form a barrier. The result could actually be some local acceleration of adhesion formation. Thus, although the prior art may require thrombin to produce the desired barrier layer, the presence of the thrombin in the barrier layer and in the co-applied sealant (in the case of the two part adhesion prevention process of WO 98/02098) may have an opposite and unwanted effect. Further, from an immunological perspective there is a possible risk, after an initial thrombin sensitization, to a more pronounced immune response upon a future challenge, e.g., in future surgery using fibrin sealant incorporating thrombin. Finally, recent evidence suggests that thrombin retained with fibrin sealant on blood vessels, even intact vessels, permeates the vessel wall and is measurable in the bloodstream. This could increase the risk of adverse thrombogenic events, especially at the higher doses of thrombin suggested in prior art sealant/barrier methods. Thus, preferred methods of preventing or reducing the incidence of post surgical adhesions involve the formation of a fibrin polymer either from a fibrin monomer composition where no added exogenous thrombin is required, or from a fibrinogen/thrombin system where the thrombin is separated, removed or otherwise not applied to the patient following the appropriate catalysis o the fibrinogen-to-fibrin polymer conversion. Although this method is described with regard to being substantially free of exogenous or added thrombin, it should be appreciated that it may apply to other enzymes capable of catalyzing the cleavage of fibrinopeptide A and/or B from fibrinogen, as well. Although the other enzymes known in the art, e.g., batroxobin, Ancrod and the like, do not precipitate the issues described above for thrombin but can nonetheless be removed from fibrin polymer-forming compositions where a sealant/barrier substantially free from any foreign proteins is desired.

Since materials most natural to the patient are now believed to provide a more natural biologic response, methods of preventing or reducing the incidence of post surgical adhesions using a fibrin sealant/fibrin polymer which is substantially free from proteins, enzymes or polymers foreign to the patient are part of the present invention. Although the exact mechanism is not understood, it is possible that minimizing foreign agents minimizes the inflammatory response of the wounded tissues where post surgical adhesions are expected. Although some workers in the prior art have attempted to use antiinflamatory agents to prevent or reduce the incidence of post surgical adhesions, others working with fibrin sealants in post surgical adhesion methods have ignored the antiinflamatory theory and essentially viewed the sealants as physical barriers. In accordance with the present invention fibrin sealants/polymers substantially free from proteins, enzymes or polymers exogenous to the patient provide the physical barrier aspects while reducing the possibility of accelerating adhesion formation which may otherwise result from an inflammatory response.

In accordance with this autologous aspect of the present invention, it should be understood that the term "substantially free" refers to the fact that the sealant materials applied to prevent or reduce the incidence of post surgical adhesions contain less than 10% by weight and preferably less than 5% and more preferably less than 1% and most preferably between 0.5 and 0% of proteins, enzymes or polymers which are foreign or exogenous to the patients. Pursuant to this autologous method the fibrin sealant/fibrin polymer can be applied as autologous fibrinogen and autologous thrombin. This fibrinogen/thrombin sealant may also include autologous stabilizers or antifibrinolytics such as is described in U.S. Ser. No. 60/069,652 filed Dec. 9, 1997. If a proteolytic enzyme other than autologous thrombin is used to treat the fibrinogen, then the fibrinogen applied needs to be at least 90% free of this enzyme as described above. Similarly, if a fibrin monomer composition is applied it should be at least 90% free of the enzyme used to prepare the autologous fibrin monomer from autologous fibrinogen.

Further to these autologous methods, it has been found in accordance with the present invention that one or more additional autologous plasma proteins help provide a more chemically natural clot material and, thereby, enhanced results in preventing or reducing the incidence of post surgical adhesions. Autologous plasma proteins, preferably selected from those which would otherwise be present in a natural clotting process can be added to the sealant components before or during application to the surgical wound site in accordance with the present methods. Alternatively, they can be coharvested in the process of producing the one or more autologous blood components which will form the fibrin sealant. For example, a process to prepare autologous fibrinogen nay result in a natural cocktail including the an may be co-applied with the monomer. GB 97/11927.5 describes such compositions useful as fibrin sealants for hemostasis and seating. These have now been found to additionally function as natural barriers to adhesion formation without the need for preforming sheets ex vivo, using multiple sheets or layers, or adding polymers. Thus, autologous blood components, such as fibrin monomer, may include one or more autologous proteins which are added or co-harvested and are selected from the group consisting of prothrombin, factor XIII (activatable), plasminogen, fibronectin, antithrombin III and factor X. Preferably, compositions useful herein include about 10–30 mg/ml of autologous fibrin monomer, about 10–40 $\mu$g/ml of autologous prothrombin and about 100–200 $\mu$g/ml of plasminogen. They may further include 5–100 $\mu$g/ml of activable factor XIII and/or 45–150 $\mu$g/ml of fibronection and/or 2.0–7.0 $\mu$g/ml of factor X and/or 50–200 $\mu$g/ml of antithrombin III, all such components being autologous to the patient receiving the anti-adhesion treatment.

Also, it is now understood that certain processing steps may have an effect on the efficacy of the prevention of post surgical adhesions using fibrin polymers. For example, some fibrin sealants are subject to processes design to reduce the risk of viral infection. "Solvent/detergent" processes are reportedly helpful in reducing viral risk for certain viruses. Also, some fibrin sealant precursors are lyophilized so as to be commercially available in a reconstitutable, powder form. Many sealants processed under these relatively harsh conditions tend to "denature" the important plasma proteins, e.g., fibrinogen and thrombin. This, in turn, may explain the relatively high concentrations of such proteins in prior art sealant methods to facilitate polymerization. Even at these higher concentrations, polymerization is slow compared to components not subject to the solvent/detergent processes. To prevent or reduce the incidence of post surgical adhesions it is clear that fibrin polymers formed of blood proteins which have not been subjected to solvent/detergent processing and/or lyophilization provide better results. Process steps believed to chemically and/or biologically denature clot-forming blood proteins include the use of harsh chemicals and extreme temperatures.

The present invention teaches fibrin sealants/fibrin polymers which are chemically more akin to natural clots in that they have fewer exogenous materials and/or have been subjected to less extreme processing. The physical structure may also closely resemble the natural clot or may take on a different structural make-up as described in a copending application U.S. Ser. No. 60/136,902 filed concurrently herewith.

EXAMPLE 1

A fibrin sealant in accordance with the present methods was prepared as described by Edwardson et al. in U.S. Pat. No 5,750,657 and using a process and apparatus as disclosed by Holm, inter alia, in U.S. Pat No. 5,741,428, U.S. Pat. No. 5,603,845, U.S. Pat. No. 5,824,230 and U.S. Pat. No. 5,958,253.

Freshly drawn anti coagulated whole blood (120 ml plus 17 ml 4% trisodium citrate USP) was centrifugally separated and the resulting plasma (60 ml) reacted with biotin-batroxobin for 10 minute at 37° C. The acid soluble fibrin I polymer produced was isolated by centrifugation and dissolved in 3.5–5.2 ml 0.2M sodium acetate buffer (pH4) containing calcium ions.

Approximately 6 ml of concentrated fibrin I (20±2 mg/ml) which is stable for several days at −20° C. resulted. Trace amounts of biotin-batroxobin were removed by addition of freeze-dried avidin covalently coupled to agarose, which hydrates the fibrin I. Within 5 minutes the biotin-batroxobin:avidin-agarose was removed by filtration and the concentrated fibrin I monomer was transferred to the desired applicator devices for use in the following experiments.

The resulting F1 monomer solution was co-applied with a carbonate/bicarbonate buffer (pH10) in a ratio of 7:1 (F1:pH10).

EXAMPLE 2

This study was constructed to assess the effect of the fibrin monomer sealant of Example 1 (hereinafter "F1 monomer sealant") on post-surgical flexor tendon adhesion formation in a rabbit experimental model. Further subdivision into mobilized and immobilized postoperative groups allowed assessment of any synergy between the F1 monomer sealant and a method well documented to reduce adhesion formation, namely early active mobilization.

Materials and Methods
Animal Model and Surgical Procedure

Murex Lop rabbits were used for this study. They were of equal sex distribution and the body weight ranged from 2500 to 4500 grams. There was one death prior to end point assessment making the total number of rabbits 19 (9 male, 10 female). The animals were obtained at least seven days prior to surgery from Murex BioTech Ltd (Dartfort, Kent) to allow for acclimatization. Throughout the study period they were housed in single cages and fed and watered ad libitum. Regular assessment of the animals' general condition and surgical wound were carried out in accordance with the U.K. Home Office "Guide for the Care and the Use of Laboratory Animals" 1996.

The surgical procedure was carried out in a fully equipped operating theatre, which was "Good Laboratory Practice" compliant. Induction of anaesthesia was by Hypnorm® (Janseen Copenhagen, Denmark, 0.2 ml/kg, im) followed by Diazeparm (Phoenix, 0.5 ml/kg, iv). Maintenance was via an anaesthetic mask, which delivered 2% halothane (Zeneca) and oxygen flowing at 21/min. The condition of the anaesthetised animals was continuously monitored using a pulse and oxygen saturation probe. Recovery from anaesthesia was encouraged with pure oxygen delivery via the facemask.

Prior to the start of the procedure the left front paw's flexor aspect was shaved with hair clippers. After anaesthetic induction the operative site was prepared with chlorhexidine in alcohol and iodine in alcohol scrubs. The field was isolated with sterile drapes. With the aid of an operating microscope, the second and fourth digits of the left front paw were longitudinally incised over the base of the proximal phalanx. Blunt dissection in the midline revealed the digital sheath and its tendinous contents. The sheath was then opened between pulleys A2 and A3 (a point corresponding to the middle of the proximal phalanx). Flexor digitorum profundus was exposed (FIG. 1). This long flexor tendon of digits two and four then received a standard surgical injury on its volar aspect with a 15 blade. The injury measured 5 mm in length and exposed the core substance of the tendon. Prior to wound closure the flexor digitorum profundus wounds of digit two and four were either treated with F1 monomer sealant (FIG. 3) or received no treatment. Application of F1 monomer sealant (between 0.1–0.4 mls) was through a variable fine jet applicator as disclosed in WO 97/20585 and WO 98/20931. The resultant coating was allowed to polymerise in air for 3 minutes and the injured tendon was then returned to the base of the wound. The operated untreated digits also received 3 minutes of air exposure. All second digits were immobilised with the additional surgical procedure of proximal tendon transaction. This was performed through a transverse skin incision just distal to the carpal tunnel. Both flexor digitorum profundus and flexor digitorurn superficialis to digit two were sharply transacted in the palm thus immobilising the digit. All skin incisions were closed with subcuticular interrupted horizontal mattress sutures (4/0 Vicryl (Ethicon)). The wound was then dressed with Cicatrin® (Wellcome) anti-microbial powder and sprayed with Opsite® (Smith and nephew). No external dressings were applied. All animals received buprenorphine (0,01–0,05 mg/kg) for postoperative analgesia. After recovery animals were allowed to move about as normal in their cages. At 14 days post surgery, the animals were euthanased using a lethal barbiturate intravascular injection.

Biomechanical Assessment of Adhesion Development

Adhesion development was assessed by the use of a tensiometer in all operated groups. In addition the animals unoperated right front paw (digits two and four) were assessed in the same way so as to provide an unoperated control group for comparative analysis. Double blind biomechanical assessment was therefore conducted on 5 groups.

Group 1 Unoperated controls.

Group 2 Immobilised (digit 2) operated and F1 monomer sealant tested.

Group 3 Mobilised (digit 4) operated and F1 monomer sealant tested.

Group 4 Immobilised (digit 2) operated and no further treatment.

Group 5 Mobilised (digit 4) operated and no further treatment.

The tensiometer (NE Holm A/S, Denmark) measured the force in grams required to pull the flexor digitorurn profundus tendon from its sheath. The freshly culled animals' front left and right second and fourth digit were each dissected and the flexor digitorum superficialis and flexor digitorum profundus were transacted proximal and distal to the operative injury site. The proximal dissection culminated in transacting the two tendons approximately 15 mm proximal to the mouth of the digital sheath. The distal dissection culminated in the flexor digitorum profundus tendon being transacted between the A3 and A4 pulley making sure that this was proximal to the insertion of the vincular vessels. The proximal stump of the flexor digitorurn profundus tendon was then transfixed with a silk 2/0-stay suture. With the nail of the relevant digit held rigid in a clamp, the silk tie was then connected to the tensiometer. The force required to pull the tendon free from the sheath was recorded in grams and was indicative of adhesion build-up.

Statistical assessment of the observed data was carried out using a robust regression technique in a Stata Release 6 statistical software package. This analysis accounted for the structure of the data, which consisted of several measurements per animal. This technique specifies that there is inter but not necessarily intra animal observation independence. Robust estimates of the standard errors of regression coefficients were calculated using the Huber/White/sandwich estimator. This takes into account the potential lack of independence from the same sample. The residual variances were not constant between groups on the original scale of measurement. They were therefore not normally distributed. The statistical analysis was therefore performed after applying a $\log_{10}$ transformation. Regression analysis obtained estimates of geometric mean tension and 95% confidence intervals per group. To obtain these values the coefficients and confidence intervals on the logarithmic scale were transformed back into the original scale of measurement (Table 1 and 2). The raw data has been graphed on a box and whisker plot (Sigma Plot version 4.0). The boxes correspond to the interquartile range (the central 50% of the data) with an internal line to mark the median. The mean is represented with a dotted line. The length of the whiskers are 1.5 times the interquartile range. Values outside the whiskers have been plotted individually.

Results

This study used 20 rabbits. One died prior to biomechanical assessment. They were randomly assigned to one of four treatment groups or an unoperated control group. The potential maximum number of observations of the 19 rabbits was 76, four per rabbit. However out of these only 67 were suitable for statistical analysis (88%) due for example to the tendon snapping in the mobile group, or incomplete distal transaction prior to tensiometer pull. Statistical assessment was therefore performed on the following number of tendons per group. Group 1 (n=36) Group 2 (n=7) Group) 3 (n=6) Group 4 (n=10) and finally Group 5 (n=8).

Figure 7:
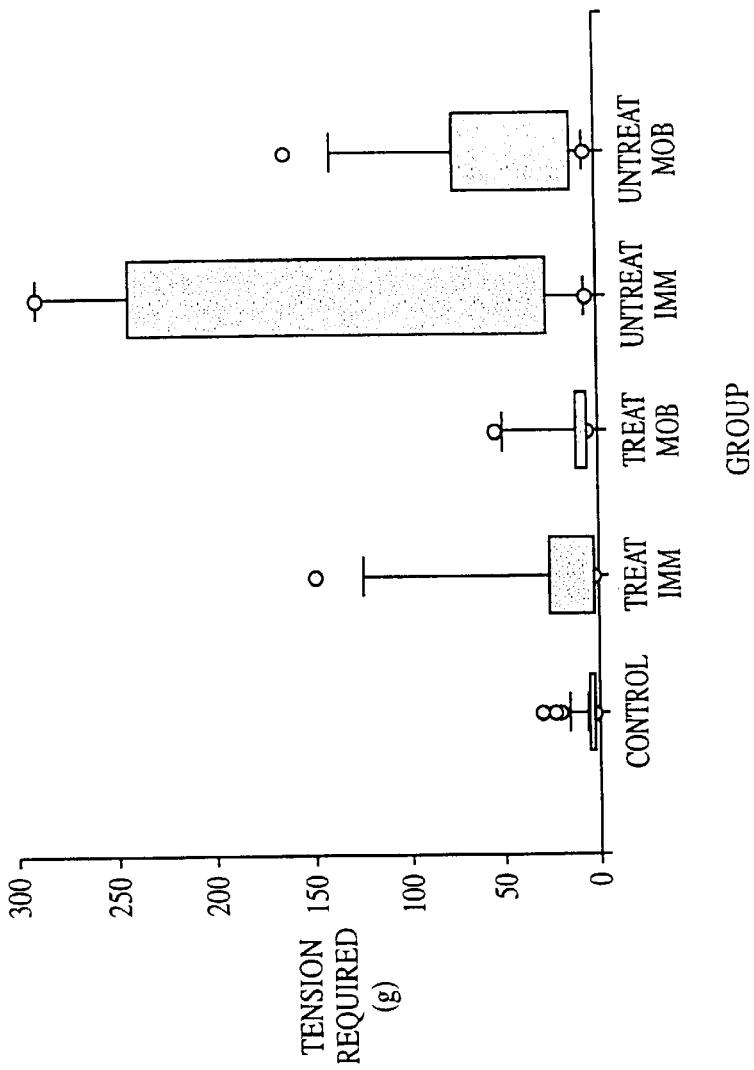
FIG. 7 Is a graph representing the raw tensiometer pulls mean value for each group in Example 2.

The raw tensiometer pulls mean value for each group is graphically represented in FIG. 7. Interpretation of the raw data revealed an overall reduction in pull required to remove the tendon from its sheath by 75.6% when comparing the total treated F1 monomer sealant groups. When separated into mobile and immobile the reduction from untreated to treated groups was 79.7% and 76.8% respectively.

As previously stated the group data was not normally distributed. Meaningful interpretation of the raw data required application of a logarithmic scale. Table 1 shows the geometric mean tension values and 95% confidence intervals for the mean per group). Comparison was made between operated groups and unoperated controls using robust regression analysis. This analysis demonstrated no statistical difference when comparing the F1 monomer sealant treated groups (immobilised p=0.42, and mobilised p=0.47) with the normal unoperated control pulls. This implies there was no significant difference in adhesion formation between F1 monomer sealant treated injuries and unoperated controls. There was however a highly significant difference with comparisons made between the operated untreated groups and the unoperated controls (immobilised p<0.001, and mobilised p<0.01). This indicated that without treatment with F1 monomer sealant, surgical injury produced significant increases in adhesion formation, as evaluated by tensiometer pull in comparison to the unoperated controls. Further analysis of the data shows that between the operated groups with the same type of post operative mobilisation, the addition of F1 monomer sealant makes a significant difference (difference between F1 monomer sealant immobilised and untreated immobilised p=1.03, difference between F1 monomer sealant mobilised and untreated immobilised p=5.03). After performing regression analysis on the $\log_{10}$ of the raw data, percentage change in mean tension from unoperated control side was as follows:

Group 2 Immobilised operated and F1 monomer sealant treated (increased by 72%)

Group 3 Mobilised operated F1 monomer sealant treated (increased by 39%)

Group 4 Immobilised operated and no further treatment (increased by 980%)

Group 5 Mobilised operated and no further treatment (increased by 490%)

From these data it can be concluded that both the mobile and immobile F1 monomer sealant treated groups were not significantly different to unoperated control group (P=0.47 and P=0.42 respectively Table 2). The raw data graph (FIG. 7) shows that F1 monomer sealant works in combination with active mobilisation to reduce the force required to pull the tendon from the sheath, indicating a considerable reduction in adhesion generation in treated cases. This is contrasted with the comparison made between the unoperated control group and the operated untreated group. Both the mobile and immobile untreated groups form significantly more adhesion than the unoperated control (P<0.001 respectively (Table 2)). Again the raw data graph does show the benefits of mobilisation in the reduction of adhesion formation (FIG. 7).

TABLE 1

The geometric mean tension and 95% confidence intervals for the mean per group

| Group | Geometric Mean Tension | 95% confidence interval for the mean |
|---|---|---|
| Unoperated control | 1.5 | 0.4 to 2.9 |
| Vivostat Immobilised | 4.7 | −1. to 26.3 |
| Vivostat Mobilised | 3.2 | −0.5 to 12.6 |
| No Treatment Immobilised | 45.1 | 13.0 to 142.0 |
| No Treatment Mobilised | 23.4 | 7.1 to 66.3 |

TABLE 2

P Values from the robust regression analysis comparing every pair of group means.

|  | Unoperated control | Vivostat Immobilised | Vivostat Mobilised | No Treatment Immobilised |
|---|---|---|---|---|
| Vivostat Immobilised | 0.42 | | | |
| Vivostat Mobilised | 0.47 | 0.77 | | |
| No Treatment Immobilised | <0.001 | 0.03 | 0.004 | |
| No Treatment Mobilised | <0.001 | 0.13 | 0.03 | 0.42 |

EXAMPLE 3

The clinical performance of fibrin sealants is influenced by physical properties such as elasticity, tensile strength, and ability to adhere to human tissue. These properties are related to the internal structure of the fibrin sealant that builds as it polymerises. Analysis of the minimum polymerisation time to achieve a functional fibrin clot is clinically important. Instant tissue-fibrin sealant adhesion is desirable to ensure that the fibrin sealant functions on contact and remains at the site of application without being washed away by blood or displaced by movement of the target tissue (e.g., the heart or lungs). The physical characteristics of fibrin sealants are related to the extent of fibrin crosslinking. Determination of the polymerisation rate allows calculation of the minimum time required to produce a functional clot. The adhesion characteristics to vital human tissue and kinetics of polymerisation between 20 and 300 seconds post-application of Vivostat™ Fibrin 1 monomer based sealant have been analysed and compared to those obtained for two conventional fibrin sealants, Tissucol® and Beriplast®. Mathematical analysis of the experimental data revealed that polymerisation of Vivostat™ sealant followed first order kinetics whereas that of Beriplast® and Tissucol® followed second order kinetics. This study demonstrates that Vivostat™ sealant polymerises faster than conventional fibrin sealants.

1. Materials and Methods

Solutions were prepared from fresh blood donations as described in Example 1 and used within I hour. Sealant was delivered using the Spraypen™ applicator in combination with the automated Vivostat™ application unit as disclosed by Holm et al. in WO 97/20585 and WO 98/20931. Conventional fibrin sealants Tissucol® (Baxter) (1 ml and 2 ml kits) and Beriplast® (Aventis) (1 ml and 3 ml kits) were prepared and applied according to the manufacturers' instructions. Tissucol® and Beriplast® were applied using the Duploject® and Pantaject® applicators, respectively, fitted with a needle or a spray head.

Torsion rheometry experiments were performed using a controlled stress rheometer, Carri-Med CSL 100 auto gap. Approximately 0.5 ml of fibrin sealant was applied on to the bottom of the rheometer. The top was a 2 cm diameter fine-hatched plate and the sample platform consisted of a 2 cm diameter fine-hatched plate over a Peltier baseplate. The temperature of the rheometer was set at 37° C. Oscillation experiments were performed using a constant oscillation torque of 15 $\mu$Nm at a frequency of 0.1 Hz for 11 minutes.

Figure 3:
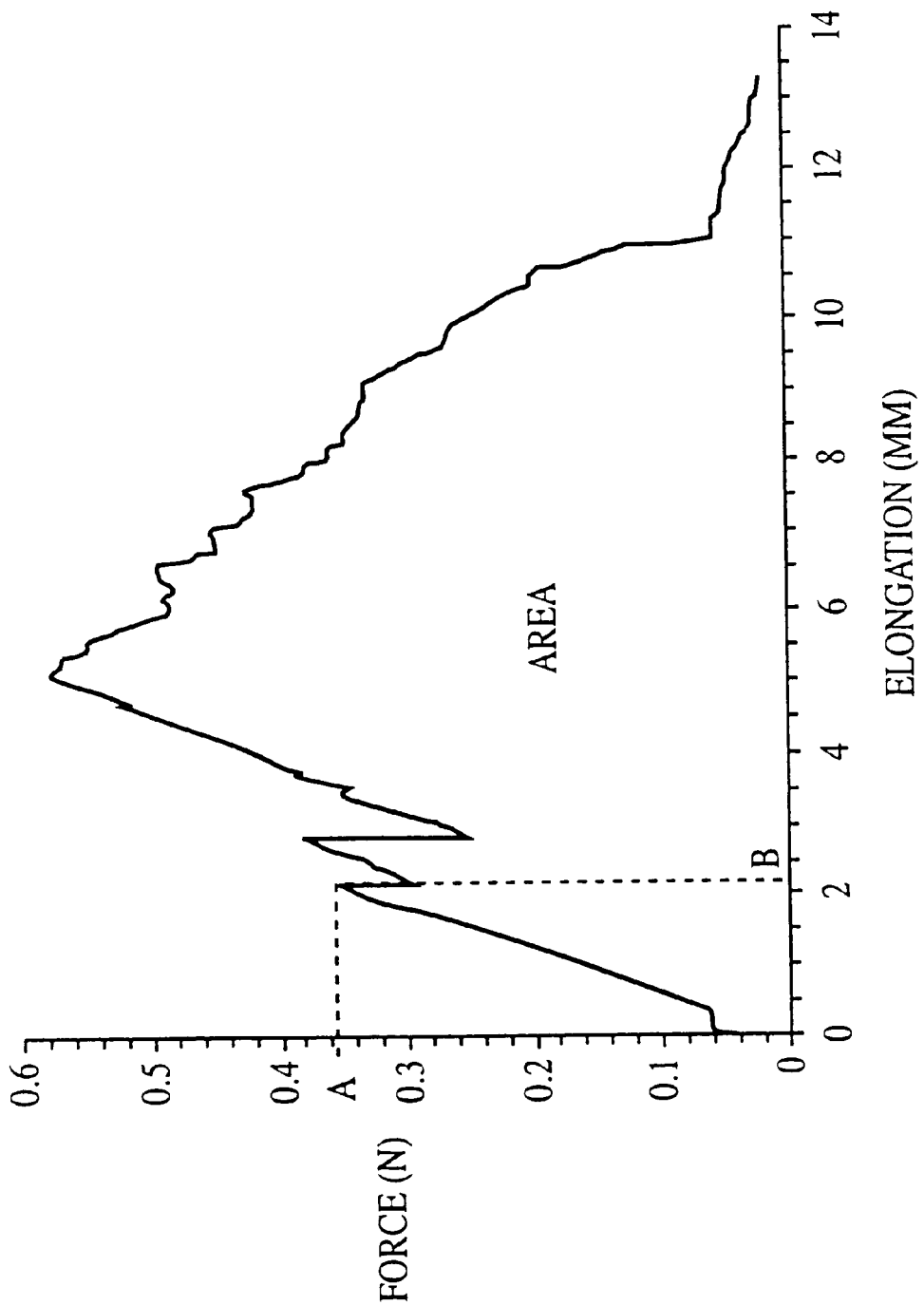
FIG. 3 Is a graph illustrating the adhesion experiment of Example 3.

Adhesion experiments were performed using a recently described model involving use of vital human tissue (Kjaergaardetal, Eur. Surg. Res. 1999). The human tissue samples were greater saphenous vein grafts left over from coronary artery bypass grafting. To ensure tissue vitality, all samples were kept in physiological saline solution and used within 24 hours of harvesting. The vein graft was split longitudinally and the split graft was cut into 1 $cm^2$ samples that were fixed to the sample holder using Gore-Tex V5 retaining sutures. The two samples were brought into close proximity at an angle of 45°, and 0.1 ml of fibrin sealant was sprayed on the tissue surfaces, where the adventitia was exposed. The two tissue samples were brought into contact without external pressure and were left polymerised until the adhesion experiment began. Tests were performed using a Nene universal testing machine model M5 at a speed of 10 mm per minute. Adhesion strength defined as force divided by the cross-sectional area of the sample, adhesion energy (i.e., area under the experimental curve as seen in FIG. 3), and elongation (i.e., extension reached by the specimen) were calculated for each experiment. Mean values were calculated at each polymerisation time. Confidence intervals (i.e., 95% CI) were also calculated for each parameter as 95% CI=1.95·CV/√n, where n is the number of samples analysed and CV=6.60, 8.35, and 9.81% for the adhesion strength, extension and adhesion energy, respectively.

2. Results

Sixteen solutions, each prepared from fresh blood donations from different donors, were sprayed on to the rheometer stage, and the rheology of the fibrin clot formed was studied over a period of 11 minutes. The average fibrin I concentration was 22.20 mg/ml±12.7% (CV). Four samples of Tissucol® and Beriplas® were also analysed the rheometer.

Curve fitting analysis of dG'/dt against time revealed that the polymerisation of sealant followed first order kinetics as shown in equation (1) where t is the time, $(dG'/dt)_0$ is the value of the derivative at t=0 and k is the kinetic rate constant:

$$\frac{dG'}{dt} = \frac{(dG')}{(dt)_0} e^{-kt} \quad (1)$$

A single curve showing dG'/dt versus time was prepared averaging the values for the sixteen samples at each time point. The values obtained for k and $(dG'/dt)_0$ were $1.17-10^-{_2}\pm0.05\cdot10^{-2}$ $s^{-1}$ and $3.17\pm0.15$ pa $s^{-1}$, respectively (r=0.9926; x=0.0683).

Analogous mathematical analysis was applied to samples of Tissucol® and Beriplast® fibrin sealants. An attempt to fit the experimental data to equation (1) gave a very poor correlation (r=0.8300–0.9400). In this case, dG'/dt followed second order kinetics as shown in equation (2) where t is the time, $(dG'/dt)_0$ is the value of the derivative at t=0 and k is the kinetic rate constant in pascals$^{-1}$.

$$\frac{(dG')}{(dt)} = \frac{1}{kt\frac{1}{\frac{(dG')}{(dt)_0}}} \quad (2)$$

Kinetic parameters for Tissucol® and Beriplast® were calculated by fitting the average dG'/dt curve to equation (2). Table 3 shows the results obtained following this procedure. For conventional fibrin sealants, the mixing efficiency of the two components of the fibrin sealant had a great influence on the speed of formation of the clot. Spray delivery systems increased the kinetic rate constant by almost 43% for Tissucol® and by 18% for Tissucol®.

Figure 4:
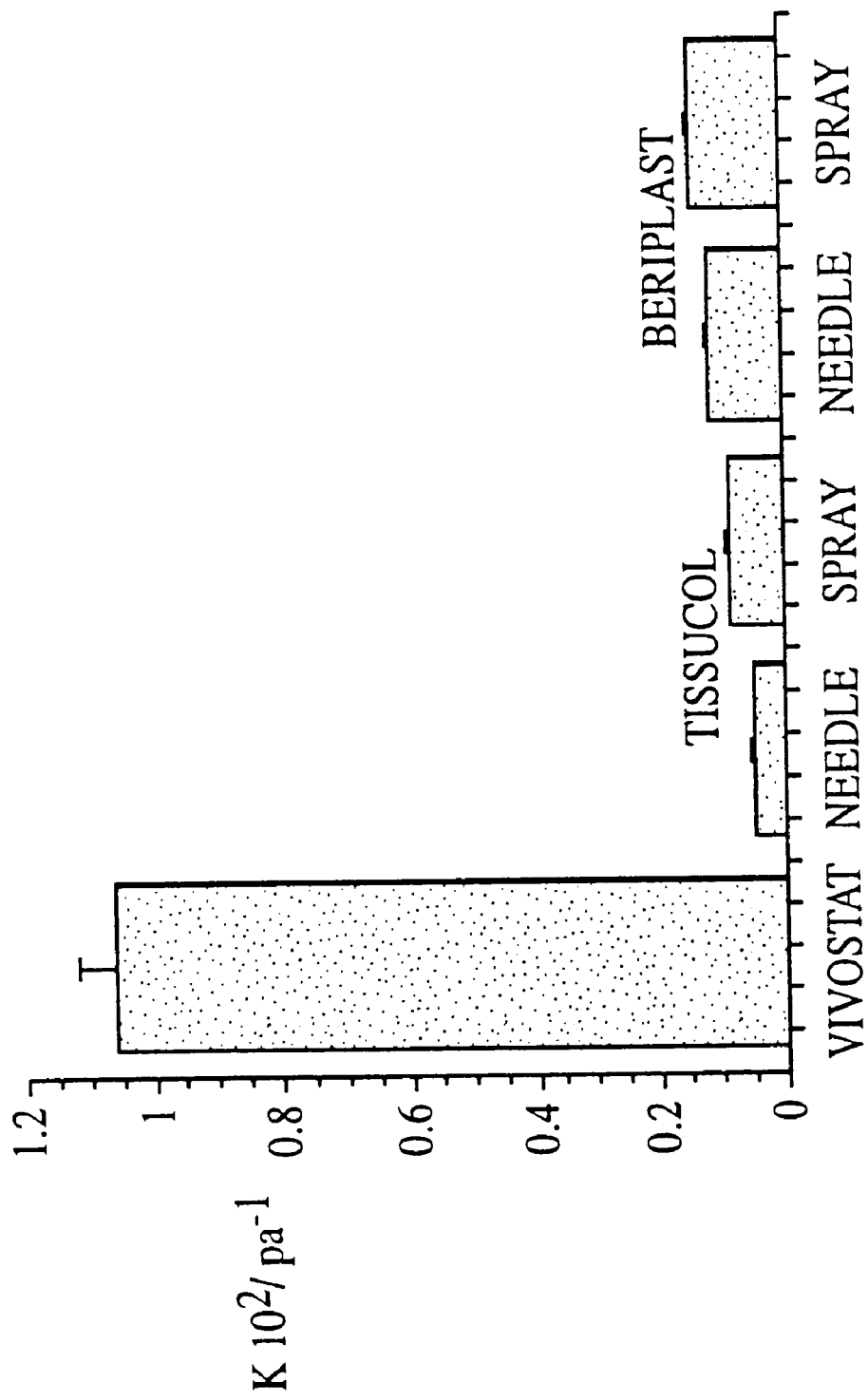
FIG. 4 Is a graph comparison of Vivostat™, Tissucol® and Beriplast® kinetic rate constants based on a second order reaction over the initial 200 seconds of polymerisation.

The kinetics of polymerisation of Tissucol® and Beriplast® were compared over the first 200 seconds of polymerisation. Over this period of time and for the sale of comparison, tile experimental curve can be fitted using the second order kinetics model represented by equation (2) with a good correlation (r=0.9974). In this case, the kinetic rate constant exhibited a similar absolute value (i.e., $k=1.06 \cdot 10^{-2} \pm 0.06 \cdot 10^{-2} pa^{-1}$) to that obtained using equation (1). Results are summarised in FIG. 4. As shown, the second order kinetic rate constant was between 6 and 20 times greater than the other fibrin sealants.

Adhesion experiments were performed on samples of sprayed fibrin sealant in order to compare similar application systems. Most of the samples showed a first breaking point (i.e., intersection of points A and B, see FIG. 3) before the maximum force was reached. This point was detected by a sudden reduction in adhesion force (FIG. 3) and was visually observed as a partial breaking of the sample. This represents the limit of the elastic character of the sealant and the first failure of the system, which has clear implications from a clinical point of view. Elongation at first breaking point (i.e., elongation at B) and adhesion strength at first breaking point (i.e., force at point A divided by the cross-sectional area) were measured for each sample. Maximum adhesion strength and elongation as well as adhesion energy (i.e., area under the experimental curve) were also calculated. Two identical adhesion experiments were prepared at each time point and the mean value recorded for each sealant sample. Results are summarised in Tables 4–6.

Figure 5:
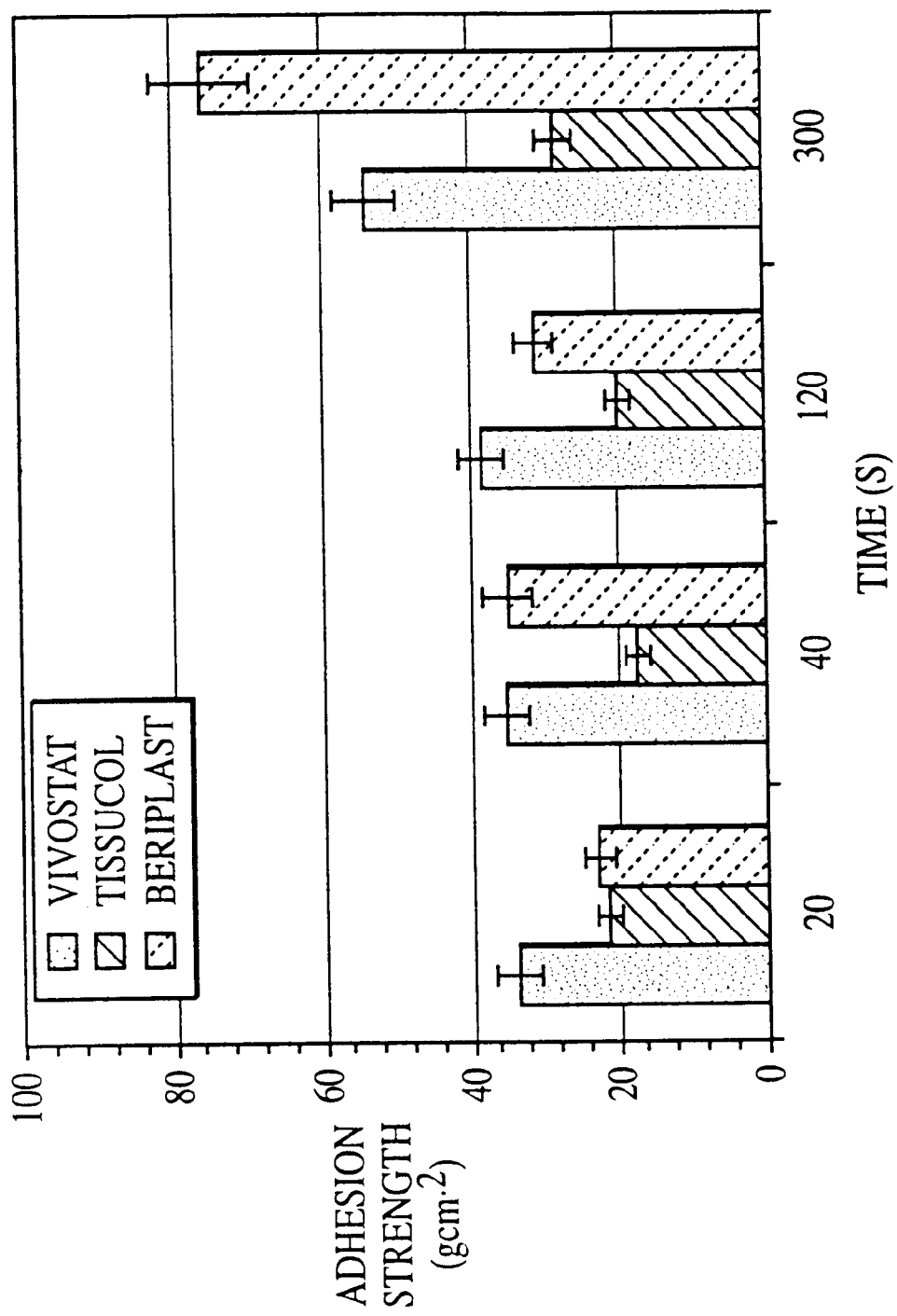
FIG. 5 Is a graph illustrating adhesion strength at first breaking point at various polymerisation times for of Vivostat™, Tissucol® and Beriplast®.
Figure 6:
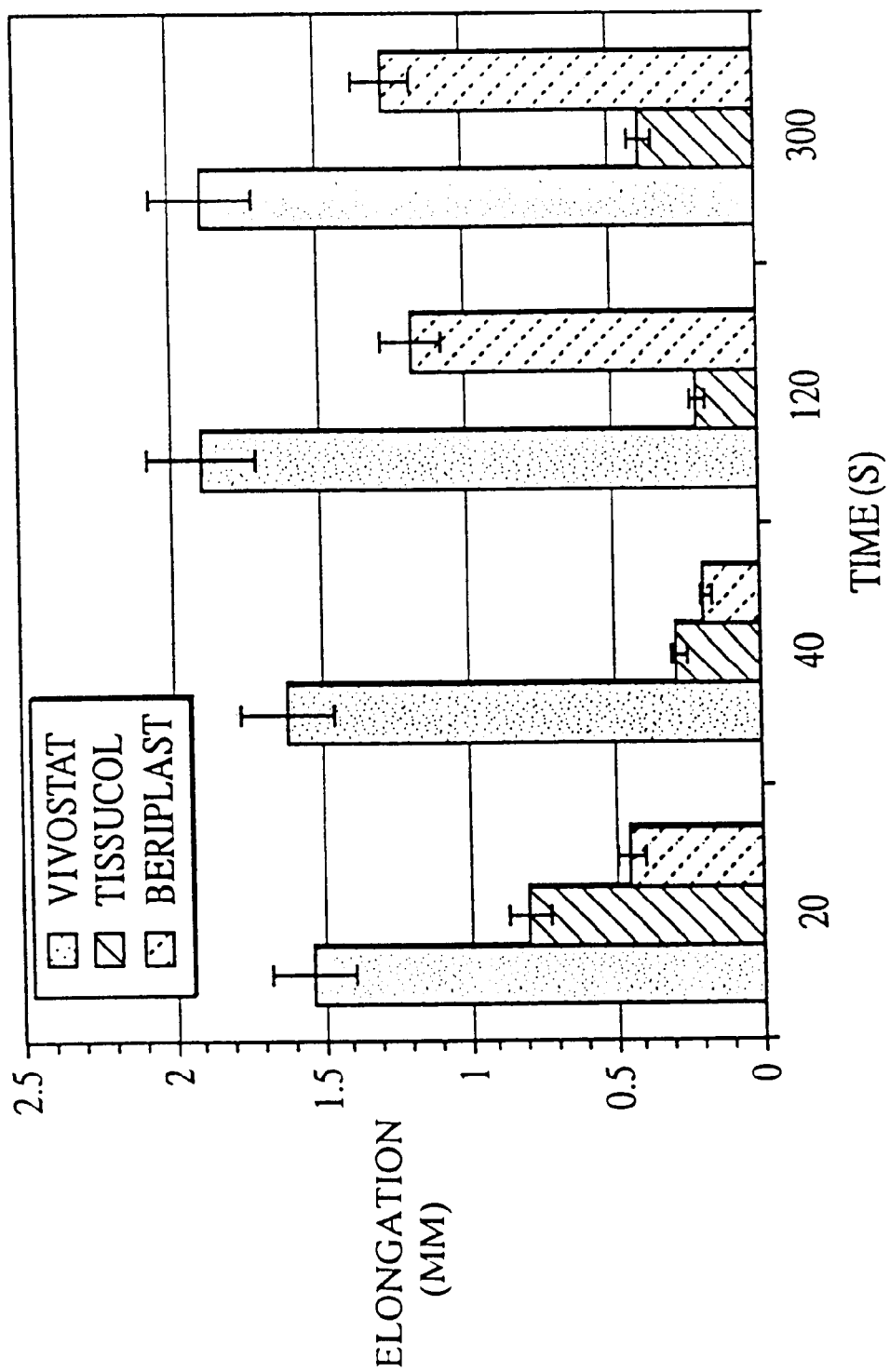
FIG. 6 Is a graph illustrating elongation at first breaking point at various polymerisation times for Vivostat™, Tissucol® and Beriplast®.

Reached a high degree of elasticity much faster than either Tissucol® or Beriplast®. This is consistent with the kinetic analysis showing that the polymerisation rate was much faster than that of competitor products. As a result, superior instant adhesion to tissue (FIG. 5) as well as better elastic characteristics (FIG. 6).

TABLE 3

Kinetic parameters and regression analysis correlation for Tissucol ® or Beriplast ® fibrin sealants

| Applicator | $(dG'/dt)_o/pa\ s^{-1}$ | $k\ 10^3/pa^{-1}$ | r | $x^2$ |
|---|---|---|---|---|
| Tissucol ® | | | | |
| Needle 3.20 | 14.15 ± 0.43 | 0.48 ± 0.02 | 0.9893 | |
| Spray | 54.19 ± 4.71 | 0.84 ± 0.04 | 0.9934 | |

TABLE 3-continued

Kinetic parameters and regression analysis correlation for Tissucol ® or Beriplast ® fibrin sealants

| Applicator | $(dG'/dt)_o/pa\ s^{-1}$ | $k\ 10^3/pa^{-1}$ | r | $x^2$ |
|---|---|---|---|---|
| 5.53 | | | | |
| Beriplast ® | | | | |
| Needle 8.80 | 19.75 ± 1.65 | 1.11 ± 0.07 | 0.9739 | |
| Spray | 29.22 ± 4.35 | 0.84 ± 0.04 | 0.9615 | 6.56 |

TABLE 4

Adhesion properties ±95% CI for Vivostat ™ fibrin sealant

| | Time (seconds) | | | |
|---|---|---|---|---|
| | 20 | 40 | 120 | 300 |
| Adhesion strength (gcm$^{-2}$) | 36.35 ± 3.31 | 34.83 ± 3.17 | 37.80 ± 3.44 | 53.13 ± 4.84 |
| Elongation (mm) | 18.36 ± 2.11 | 15.73 ± 1.81 | 14.20 ± 1.63 | 11.56 ± 1.33 |
| Elongation at first break (mm) | 1.54 ± 0.18 | 1.62 ± 0.19 | 1.90 ± 0.22 | 1.88 ± 0.22 |
| Adhesion strength at first break (gcm$^{-2}$) | 33.65 ± 3.06 | 34.83 ± 3.17 | 34.67 ± 3.16 | 34.67 ± 3.16 |
| Adhesion energy (mJ) | 3.12 ± 0.42 | 2.81 ± 0.38 | 2.47 ± 0.33 | 2.99 ± 0.40 |

TABLE 5

Adhesion properties ±95% CI for Tissucol ® fibrin sealant

| | Time (seconds) | | | |
|---|---|---|---|---|
| | 20 | 40* | 120 | 300 |
| Adhesion strength (gcm$^{-2}$) | 24.94 ± 2.68 | 40.92 ± 5.26 | 65.39 ± 5.95 | 81.11 ± 7.38 |
| Elongation (mm) | 4.45 ± 0.51 | 6.38 ± 1.04 | 8.14 ± 0.94 | 11.65 ± 1.34 |
| Elongation at first break (mm) | 0.80 ± 0.09 | 0.29 ± 0.05 | 0.21 ± 0.02 | 0.39 ± 0.04 |
| Adhesion strength at first break (gcm$^{-2}$) | 21.41 ± 1.95 | 17.34 ± 3.32 | 19.37 ± 1.76 | 27.53 ± 2.51 |
| Adhesion energy (mJ) | 0.68 ± 0.09 | 1.65 ± 0.32 | 2.41 ± 0.33 | 6.29 ± 0.85 |

*Single experiment

TABLE 6

Adhesion properties ±95% CI for Beriplast ® fibrin sealant

| | Time (seconds) | | | |
|---|---|---|---|---|
| | 20 | 40 | 120 | 300 |
| Adhesion strength (gcm$^{-2}$) | 49.95 ± 4.55 | 93.61 ± 8.52 | 131.64 ± 11.98 | 168.35 ± 15.32 |
| Elongation (mm) | 6.60$^{-2}$0.76 | 4.23 ± 0.49 | 11.84 ± 1.36 | 18.48 ± 2.13 |

TABLE 6-continued

Adhesion properties ±95% CI for Beriplast ® fibrin sealant

| | Time (seconds) | | | |
|---|---|---|---|---|
| | 20 | 40 | 120 | 300 |
| Elongation at first break (mm) | 0.46 ± 0.05 | 0.19 ± 0.02 | 1.17 ± 0.13 | 1.25 ± 0.14 |
| Adhesion strength at first break (gcm$^{-2}$) | 22.43 ± 2.04 | 34.67 ± 3.16 | 30.59 ± 2.78 | 75.46 ± 6.87 |
| Adhesion energy (mJ) | 1.41 ± 0.19 | 1.58 ± 0.21 | 7.53 ± 1.02 | 7.59 ± 1.03 |

EXAMPLE 4

The purpose of this Example 4 is to evaluate the ability of three fibrin sealants in the prevention of post surgical adhesion (PSA) in the peritoneal cavity of rabbits following surgical injury to the uterine horn and the opposing ipsilateral peritoneal wall. This example evaluate syringe-applied sealants as follows:

a) the Vivostat™ fibrin I monomer-based fibrin sealant as used in the earlier examples;

b) Tissucol®, a fibrin sealant which was commercially available in Europe through Immuno AG in Austria, and which is a two component sealant system involving the coapplication of pooled human fibrinogen (in an aprotinim-containing solution) and a bovine thrombin component in a calcium chloride solution; and c) Cyroprecipitate (CYRO), a cryoprecipitate concentrated blood component containing fibrinogen from a single donor and co-applied with bovine thrombin.

The Tissucol® and CRYO were all evaluated with 4 units and 500 units of bovine thrombin.

Model

In summary a standard abrasion injury was inflicted on each uterine horn and ipsilateral peritoneal] wall, which would naturally lie in juxtaposition.

The injured areas were then held apposed using positional sutures, placed outside the experimental site, with treated sites separated by a layer of fibrin sealant. Experimental sites were then left in vivo for the length of recovery time dictated by the study protocol. Due to the level of injury induced and injured surfaces being apposed this rabbit uterine horn abrasion model is a severe experimental PSA model, with a "worse case" scenario created.

To ensure that injuries of consistent standard area could be induced, templates, 25 mm×3 mm, designed to fit the uterine horn or peritoneal wall, were specially constructed. Abrasions were induced using a scraper with a standard depth (1.5 mm) which fitted the exact area of the template. With the additional parameter of using a set number of scrapes for each injury site, injuries were maximally standardised within the limits or biological variation.

Uterine horns were chosen as the experimental site, together with the peritoneal wall, due to their size, structure and location within the peritoneal cavity. Heavy handling of tissues has been shown to induce PSA formation (Boys, 1942; Connolly & Smith, 1960) and hence excessive tissue handling needed to be avoided. In addition, ex-breeding rabbits were also chosen for these investigations due to their large size facilitating appropriate procedures.

Procedure

Premedication was administrated with hypnorm (Fentanyl citrate 0.315 mg/ml and fluanisone 10 mg/ml. Supplied by Janssen Saunderton, High Wycombe, Buckinghamshire.) (0.2 ml/kg body weight intramuscular) to the right gluteous maximus muscle.

Surgical anaesthesia was induced with hypnorm (0.3 ml/kg body weight intramuscular) and diazepam (5 mg/ml diazepam. Supplied by Phoenix Pharmaceuticals Limited, Gloucester.) (2.5 mg/kg body weight intravenous). Full sterile operating procedures were observed. Particular attention was paid to the washing of surgical gloves in sterile water to remove all traces of particulate matter (starch, powder) which might, if transferred to the operative site, induce granuloma or adhesion formation.

Fur was shaved from the surgical area and the area scrubbed with alcoholic chlorhexidine followed by iodine. Laparotomy was performed using cutting diathermy, by a single incision in the midline, from lower liver margin to the level of the iliac fossa, through skin and muscle to peritoneum, which was divided with scissors. Retraction was applied to laparotomy wound edges to allow access to uterine horns.

Experimental areas were selected on the serosal surface of each uterine horn and corresponding internal ipsilateral surfaces of the peritoneum, which would naturally lie in juxtaposition with each other. A standard template, constructed specifically either for the uterine horn or peritoneal wall, was placed on the selected areas and each area abraded with the sharp edge of a scraping tool. A standard number of 10 scrapes was used to cause homogeneous punctate bleeding but not so far as to cause frank contiguous hemorrhage. Hence a standard, and reproducible injury was produced in each case.

Single throws of Stannius positional suture (Ethibond 6/0 or similar) were placed 5 mm outside each end of abraded areas (peritoneal wall and uterine horn). These sutures passed only through the serosa of the peritoneum and corresponding uterine horn. For control groups, sutures were tightened to bring the two juxtapositional abraded areas together and maintain contact between the two areas. Timing was commenced from this point. For treated groups positional sutures were tightened to bring the two abraded areas close together but not in contact and fibrin sealant was then applied to abraded areas. Sutures were then drawn together to bring the two areas into contact, using as much tension as was needed to create reasonable contact but avoiding tight sutures. Timing commenced from this point.

In groups which sampled up to 30 minutes post injury, rabbits were kept anaesthetised, in the supine position with the laparotomy incision held closed with tissue clamps. In groups which sampled from 1 hour post injury onwards, the laparotomy was closed and reopened after the relevant time period.

Laparotomy wound closure was in two layers: first with 2/0 plain catgut on atraumatic half round needle for the peritoneum and muscle layers, using transplant longflow, overunder, non-interrupted crossed sutures; and secondly with 2/0 Prolene or similar on half round cutting needle using interrupted mattress sutures for the skin. Immediately after closure of the wound, wound dressing was applied on and around the wound.

At 14 days post surgery animals were anesthetized (as for the surgical procedure). Laparotomy was reopened along the original incision with experimental areas identified and macroscopic observations recorded and photographed. The abraded area of the peritonem together with a border of unabraded tissue in excess of 5 mm and the associated uterine horn were resected.

A summary of the experimental groups is in Table 7 below.

| Treatment Group | Number of Animals | Experimental Sites | Mean Volume of Sealant Applied (ml) | Mean Fibrin I Conc$^n$ (mg/ml) |
|---|---|---|---|---|
| Control | 7 | 13 | N/A | N/A |
| Novel Fibrin Sealant (Needle Application) | 6 | 12 | 0.93 ± 0.06 | 14.90 ± 2.41 |
| Tissucol ® | 6 | Total: 11 | | 17.50–28.75 |
| 4 Units Bovine Thrombin | | 5 | 0.50 ± 0.03 | |
| 500 Units Bovine Thrombin | | 6 | 1.12 ± 0.11 | |
| CRYO | 6 | Total: 12 | | 10.64 ± 0.84 |
| 4 Units Bovine Thrombin | | 6 | 0.47 ± 0.02 | |
| 500 Units Bovine Thrombin | | 6 | 0.33 ± 0.03 | |

Results

Macroscopic Results

Figure 8:
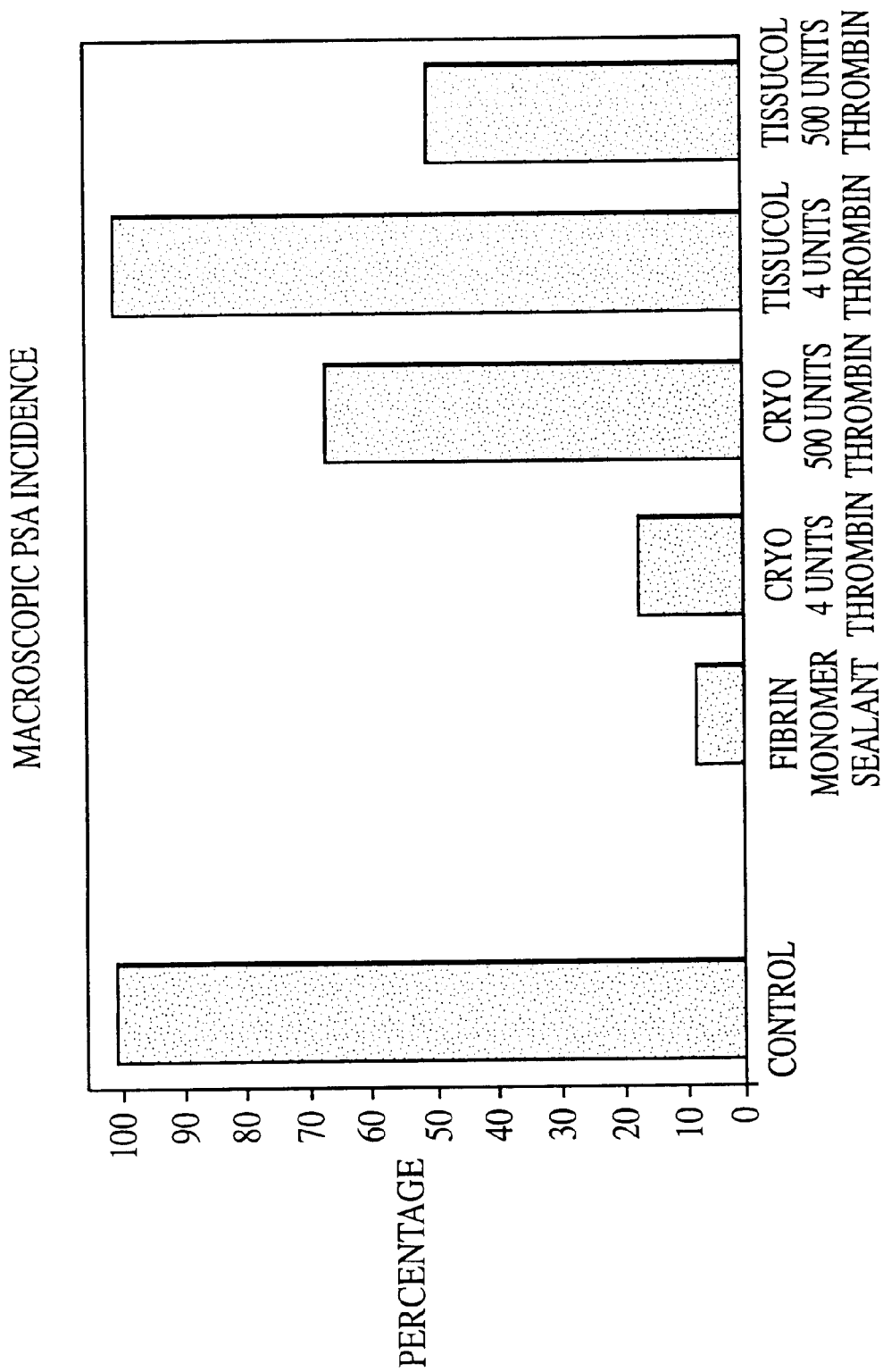
FIG. 8 Is a graph illustrating macroscopic results or Example 4.

All of the control groups (13/13) showed PSAs joining the abraded areas of the peritoneal wall and uterine horn. The macroscopic incidence of experimentally induced PSAs for treatment groups was 8.3% for Vivosta™ sealant, 16.7% CRYO 4 units thrombin, 66.7% CRYO 500 units thrombin, 100% Tissucol™ 4 units thrombin and 50% Tissucol® 500 units thrombin as shown in FIG. 8.

Microscopic Quantitative Results

Figure 9:
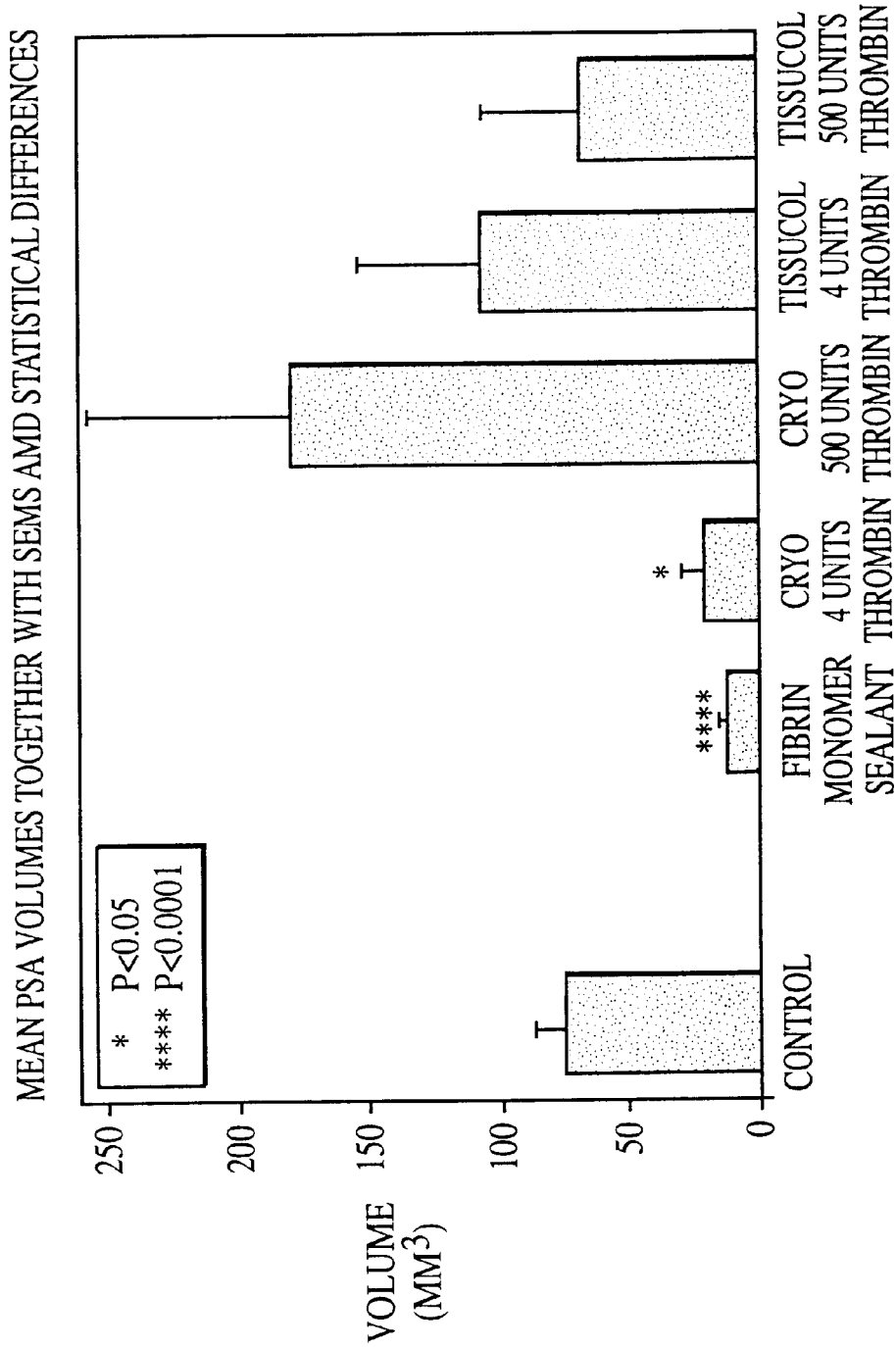
FIG. 9 Is a graph illustrating mean PSA volumes of Example 4.

Mean volumes of PSAs were 73.93 mm$^3$ for the control group, 1130 mm$^3$ for the Vivostat™ sealant treated group, 21.06 and 179.98 mm$^3$ for the CRYO treated groups with 4 and 500 units thrombin respectively and 106.12 and 69.42 mm$^3$ for the Tissucol® treated groups with 4 and 500 units thrombin respectively (FIG. 9). Significant reduction in mean PSA volume compared to controls was seen with Vivostat™ sealant (P<0.001) and CRYO (P=0.0152) 4 units thrombin treated groups only.

Figure 10:
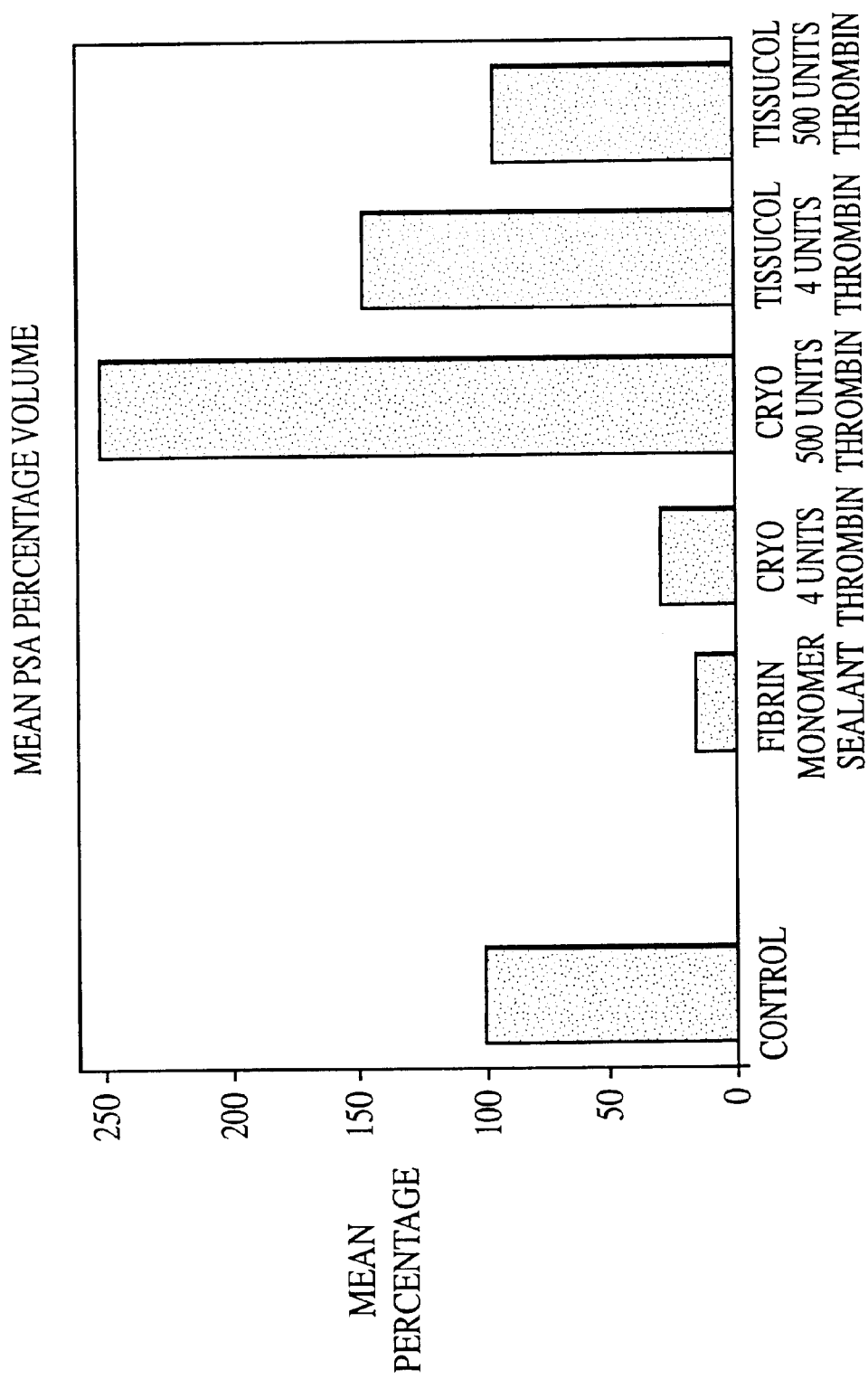
FIG. 10 Is a graph illustrating mean PSA percentage volumes of Example 4.

Assuming that the control group demonstrated 100% PSA formation, the percentage volume of PSAs for each treatment was 15.28% Vivostat™ sealant, 28.49% CRYO (4 units thrombin), 243.46% CRYO (500 units thrombin), 143.55% Tissucol® (4 units thrombin) and 93.90% Tissucol® (500 units thrombin) (FIG. 10).

Thus, the Vivostat fibrin I monomer based sealant demonstrated a superior prevention of PSAs in this model by providing a nearly 85% reduction in PSAs over the control and a significant improvement over the other sealants tested.

TABLE 8

Post Surgical Incidence/Reduction

| | % PSA | |
|---|---|---|
| Treatment | Incidence | Reduction |
| CONTROL | 100 | N/A |
| VIVOSTAT | 15.28 | 84.72 |
| CRYO + 4 units | 28.49 | 71.51 |
| CRYO + 500 units | 243.46 | −143.46 |
| Tissucol + 4 units | 143.55 | −43.55 |
| Tissucol + 500 units | 93.90 | 6.10 |

EXAMPLE 5

The aim of this example was to assess the ability of Vivostat™ Fibrin Monomer-Based Fibrin Sealant made from human blood (prepared as in Example 1) to reduce or prevent post surgical adhesions in a rat caecal abrasion model.

Experimental Procedure

Sixteen, female, Sprague Dawley rats were randomised into two groups. Each group received a standardized caecal and opposing peritoneal abrasion wounding which was either left untreated or sprayed with Vivostat™ Fibrin Sealant. The abrasions were then apposed with sutures. The animals were then allowed to recover and maintained in the animal unit for 14 days.

On day 14, the control and Vivostat™ Fibrin Sealant treated animals were euthanased and the experimental sites removed. The wounds were examined grossly, histopathologically and stereologically.

Results

The abrasion procedures resulted in an inadvertent perforation of the caecum in two animals (which was repaired using a purse string suture of 4/0 vicryl (Ethicon UK). The sites were still used for evaluation. All other surgical procedures were completed uneventfully.

There were no abnormal clinical signs observed and no mortalities.

The fibrin I solution concentrations used on the treated wounds ranged from 13.46 to 16.02 mg/ml. A mean volume of 0.79 ml Vivostat™ Fibrin Sealant was applied via the spray application to experimental sites.

Macroscopic examination of the wounds on day 14 showed adhesions in 8/8 control wounds and 0/8 Vivostat™ Fibrin Sealant treated wounds. All adhesions were dense, tenacious and fibrous.

Mean volume of post surgical adhesions measured stereologically was 89.9 mm$^3$ for control cases and 17.82 mm$^3$ for Vivostat™ Fibrin Sealant treated cases. There were fibrinous Luke connections, which were not considered to be adhesions, in the Vivostat™ Fibrin Sealant treated cases, but they were recorded as adhesion volumes for the purpose of analysis.

Conclusion

The wean volume of adhesions was significantly less (P<0.1) in the Vivostat™ Fibrin Sealant treated group compared to the control group. Vivostat™ Fibrin Sealant is an effective agent for the reduction of post-surgical adhesions when compared to controls in this rat caecal abrasion model.

This example is designed to evaluate the formation/prevention of PSAs in the stomach, colon and caecum of the pig by introducing a surgical injury to those sites similar to the rabbit uterine from model above. Pig models previously used to investigate PSAs demonstrate that pigs from PSAs in response to injury or trauma by identical pathogenesis to humans. In this example control (untreated/injured) animals were compared to those treated with of Vivostat™ Fibrin Monomer-Based Fibrin Sealant as prepared in Example 1, but wherein the sources were (a) human and (b) from the pig being treated, i.e., autologous sealant.

Pre-medication was administered using Ketamine (Ketalar-50 mg/ml ketamine hydrochloride. Supplied by Parke-Davis, Pontypool, Gwent.)(5 mgs/Kg) plus Xylazine (Rompun 2%-Xylazine hydrochloride 23.32 mg/ml (equivalent to 20 mg/ml xylazine) and 1 Mg/ml methyl 4-hydroxy-benzoate (preservative). Supplied by Bayer Plc., Animal Health Business Group, Bury St. Edmunds, Suffolk.)(1 mg/kg)) intramuscularly in the gluteous maximus muscle. At the operating suite, pigs were induced to and maintained at full anaesthesia with Halothane at 4% in oxygen and nitrous oxide delivered at 1.5 litres per minute and 0.5 litres respectively per minute via mask to the snout.

Once anaesthetised pigs were transferred to lay in the supine position on the operating table, where they were secured by soft tapes to each limb. A plastic ear tag bearing the unique pig identification number for the study was secured to one of the animals' ears. For each pig, the surgical site was shaved and scrubbed with chlorhexidine in alcohol followed by swabbing twice with iodine in alcohol. Sterile operative procedures were adhered to from this point on.

The animals were draped. Cutting diathermy and scissors were used to expose the spiral colon and the stomach through a midline laparotomy starting at the level of the distal xyphoid process of the sternum and extending distally 10–12 cms.

One area was selected on the lateral surface of the spiral colon or on the blunt end of the caecum and the medio-lateral serosal aspect of the stomach such that these areas each laid naturally against the ipsilateral peritoneal wall. Areas were then selected on the ipsilateral peritoneal wall. As with the rabbit uterine horn abrasion model, each selected area was abraded, using a template and scraper, a standardised number of 12 scrapes which caused homogeneous punctate bleeding but not so far as to cause frank contiguous haemorrhage was performed.

A single throw suture (Ethibond 0.6 or similar) was placed at each end of tile experimental site but outside of the abraded areas. These sutures passed only through the internal serosa of the peritoneum and then passed through the serosa at the respective ends of the apposed abraded areas on the stomach or colon. Sutures were tightened to bring the two apposed abraded areas close together but not in contact. For treated cases, human or porcine fibrin sealant was applied to the abraded areas (mean volume of 1.3 ml per experimental site), whereas no treatment was applied in control cases. Positional sutures were then tightened to bring the two abraded areas into close contact.

The laparotomy was closed in two layers, first with 2/0 Dexon Plus on an atraumatic half round needle for peritoneum and muscle layers, second with 2/0 Prolene or similar on half round cutting needle for skin. The first suture layer was of "transplant" longflow, over-under, non-interrupted crossed sutures, the second layer was of interrupted cruciate mattress sutures.

At 7 days post-surgery the animals were scarified and evaluated as follows. Animals were anaesthetised as for the surgical procedure. Laparotomy was reopened along the original incision, with experimental areas identified and macroscopic observations recorded and photographed.

The colon, caecum and stomach experimental sites, joined to the peritoneum by positional sutures at each end of the site, were resected. Euthanasia was achieved by high dose intravenous pentabarbitone (Expiral-Pentobarbitone sodium BP 200 mg/ml. Supplied by Sanofi Animal Health Ltd., Watford, Hertfordshire.) (150 mg/kg body weight)).

Resected tissues were trimmed of excess adipose tissue, pinned flat on stiff card, to retain a standard, lifelike tissue positional relationship, and immersion fixed in 10% neutral buffered formal saline for at least 24 hours at room temperature.

The table below summarizes the experiment.

| Treatment Group | Number of Animals | Injury Site | Number of Experimental Sites | Volume of Fibrin sealant Applied (ml) | Fibrin I Conc$^n$ (mg/ml) |
|---|---|---|---|---|---|
| Control | 3 | Stomach | 3 | N/A | N/A |
|  |  | Colon | 4 |  |  |
|  |  | Caecum | 2 |  |  |
|  |  |  | Total: 9 |  |  |
| Human fibrin sealant | 3 | Stomach | 2 | 1.56 ± 0.06 | 18.01 ± 2.29 |
|  |  | Colon | 4 |  |  |
|  |  | Caecum | 2 |  |  |
|  |  |  | Total: 8 |  |  |
| Porcine fibrin sealant | 2 | Stomach | 1 | 1.25 ± 0.05 | 19.45 ± 2.93 |
|  |  | Colon | 2 |  |  |
|  |  | Caecum | 2 |  |  |
|  |  |  | Total: 5 |  |  |

Results

All animals demonstrated general PSAs between the peritoneal suture line and underlying tissues: most frequently the omentum, ileum, caecum, spleen and liver respectively. All these PSAs were separated by blunt dissection and did not interfere with experimental sites.

All control experimental sites were adhered, many being quite severe. 5 out of the 8 sites treated with human fibrin sealant were clear of adhesions, with the remaining sites joined by either PSAs or fibrin sealant. 2 out of the 4 porcine fibrin sealant treated sites were identified as non-adhered with the other sites joined by either PSAs or fibrin sealant.

Figure 11:
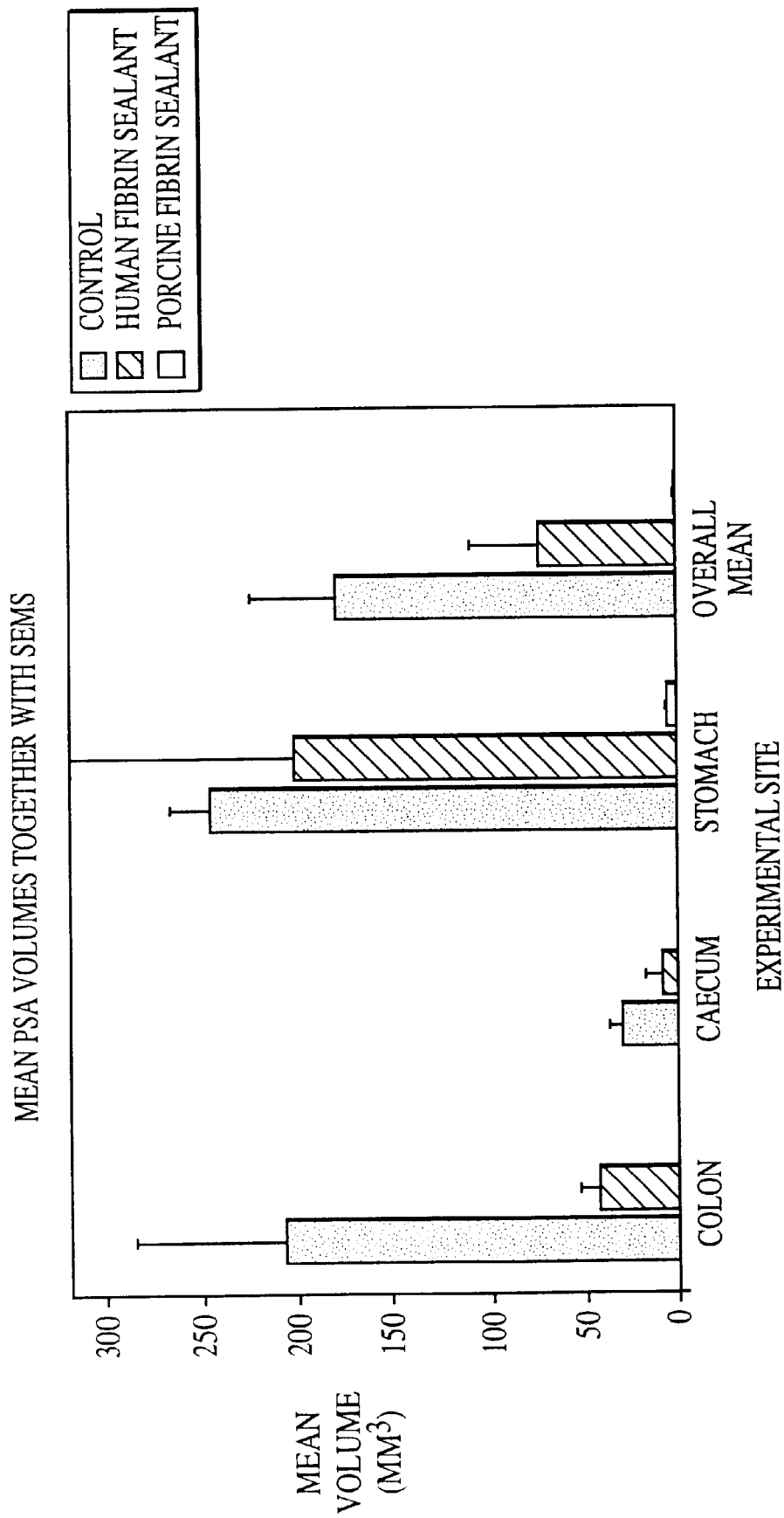
FIG. 11 Is a graph illustrating mean PSA volumes of Example 6.

Mean volume of PSAs for the control group was 207.25 mm$^3$ for the colon, 31.33 mm$^3$ for the caecurn and 248.11 mm$^3$ for the stomach with an overall mean of 181.78 mm$^3$. Human fibrin sealant treated group demonstrated mean volumes of 42.83 mm$^3$, 8.96 mm$^3$ and 204.47 mm$^3$ for the colon, caecum and stomach, respectively, with an overall volume of 74.77 mm$^3$. Whereas no PSAs were present in colon and caecum (FIG. 11) experimental sites treated with porcine fibrin sealant, with 6.25 mm$^3$ for the stomach and a group mean of 1.27 mm$^3$ (FIG. 11).

Figure 12:
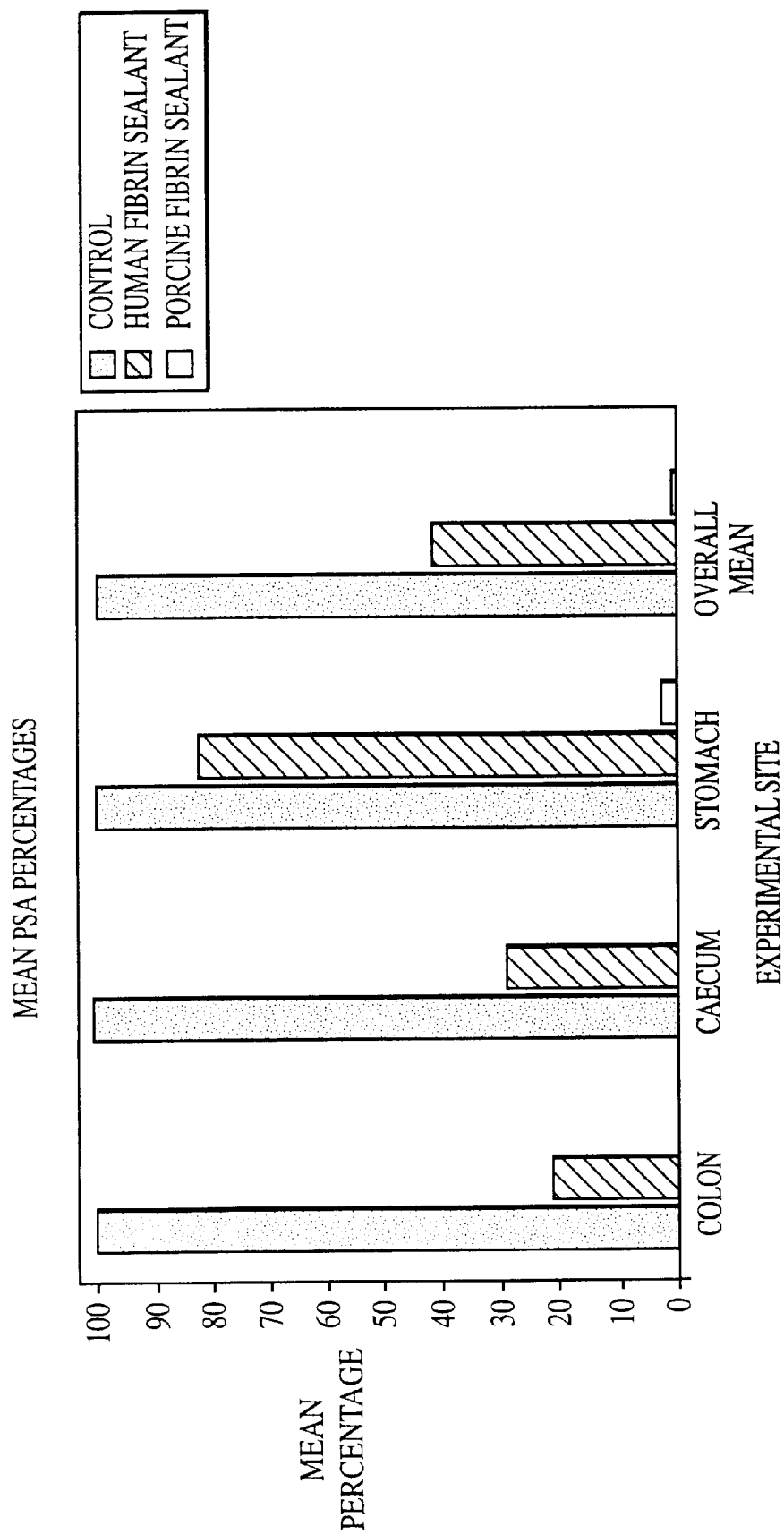
FIG. 12 Is a graph illustrating mean PSA percentage volumes of Example 6.

Assuming that the control group demonstrated 100% volume of PSA, reduction with human fibrin sealant was 79, 71 and 18% for the colon, caecum and stomach, respectively, with an overall reduction of 59%. Porcine fibrin sealant demonstrated 100% reduction for both colon and caecum, 97% for the stomach and overall 99% reduction of PSAs compared to controls (FIG. 12).

What is claimed is:

1. A method for the inhibition of post surgical adhesion formation at a surgical wound site comprising the steps of a) preparing a composition comprising fibrin monomer containing less than 10% by weight of thrombin;

b) surgically opening a peritoneal wall of an animal to create the surgical wound site; and c) applying said composition to said surgical wound site under polymerizing conditions such that a fibrin polymer is formed which inhibits post surgical adhesions of said site.

2. The method of claim 1, wherein the surgically opening comprises an operation requiring a manipulation of a uterine horn.

3. The method of claim 1, wherein the surgically opening comprises an operation requiring a manipulation of a colon.

4. The method of claim 1, wherein the surgically opening comprises an operation requiring a manipulation of a cecum.

5. The method of claim 1, wherein the surgically opening comprises an operation requiring a manipulation of a stomach.

6. A method for the inhibition of post surgical adhesion formation at a surgical wound site comprising the steps of a) preparing a composition comprising fibrin monomer containing less than 10% by weight of thrombin:

b) surgically exposing a tendon of an animal to create the surgical wound site; and c) applying said composition to said surgical wound site under polymerizing conditions such that a fibrin polymer is formed which inhibits post surgical adhesions of said site.

7. The method of claim 6, wherein the surgically exposing a tendon comprises opening a tendon sheath.

8. The method of claim 6, wherein the tendon exposed is a tendon for manipulating a terminal part of an animal corresponding to a hand or paw of a forelimb of an animal.

* * * * *